US009644197B2

(12) United States Patent
Song et al.

(10) Patent No.: US 9,644,197 B2
(45) Date of Patent: May 9, 2017

(54) FUSION PROTEIN HAVING FACTOR VII ACTIVITY

(75) Inventors: In-Young Song, Seoul (KR); Hun-Taek Kim, Seoul (KR); Bong-Yong Lee, Seoul (KR); Mahn-Hoon Park, Yongin-si (KR); Ho-Soon Lee, Seongnam-si (KR); Yun Jung Lim, Seoul (KR); Ji-Hye Lee, Seoul (KR); Seo Yeon Son, Gunpo-si (KR); Min-Sun Kim, Goyang-si (KR)

(73) Assignee: SK Chemicals Co., Ltd., Seongnam-si, Gyeonggi-do (KR)

( * ) Notice: Subject to any disclaimer, the term of this patent is extended or adjusted under 35 U.S.C. 154(b) by 0 days.

(21) Appl. No.: 13/701,333

(22) PCT Filed: Jun. 7, 2011

(86) PCT No.: PCT/KR2011/004131
§ 371 (c)(1),
(2), (4) Date: Mar. 19, 2013

(87) PCT Pub. No.: WO2011/152694
PCT Pub. Date: Dec. 8, 2011

(65) Prior Publication Data
US 2013/0236945 A1    Sep. 12, 2013

(30) Foreign Application Priority Data
Jun. 4, 2010 (KR) .................. 10-2010-0052719

(51) Int. Cl.
*C07K 14/79* (2006.01)
*C12N 9/64* (2006.01)

(52) U.S. Cl.
CPC ............ *C12N 9/6437* (2013.01); *C07K 14/79* (2013.01); *C12Y 304/21021* (2013.01);
(Continued)

(58) Field of Classification Search
CPC .................................. C07K 14/79; C12N 9/64
See application file for complete search history.

(56) References Cited

U.S. PATENT DOCUMENTS 7,125,843 B2 * 10/2006 DeFrees et al. ............. 514/13.5
2003/0221201 A1 * 11/2003 Prior .................... A61K 47/483
800/7

(Continued)

FOREIGN PATENT DOCUMENTS

CN          1400910 A      3/2003
CN          1665526 A      9/2005
(Continued)

OTHER PUBLICATIONS

Banner et al., The crystal structure of the complex of blood coagulation factor VIIa with soluble tissue factor., Nature (1996), vol. 380, pp. 41-46.*

(Continued)

*Primary Examiner* — Alexander Kim
(74) *Attorney, Agent, or Firm* — Alston & Bird LLP

(57) ABSTRACT

A fusion protein comprising factor VII (FVII) and transferrin according to the present invention has an improved specific activity of FVII compared to existing FVII fusion proteins comprising other fusion partners than transferrin, and thus can be effectively used in a therapy using FVII.

8 Claims, 4 Drawing Sheets

(52) U.S. Cl.
CPC ...... *C07K 2319/00* (2013.01); *C07K 2319/31* (2013.01); *C07K 2319/50* (2013.01)

(56) References Cited

U.S. PATENT DOCUMENTS

| | | | |
|---|---|---|---|
| 2004/0023334 A1* | 2/2004 | Prior | 435/69.7 |
| 2006/0019336 A1 | 1/2006 | Pedersen et al. | |
| 2006/0130158 A1* | 6/2006 | Turner et al. | 800/7 |
| 2007/0072271 A1 | 3/2007 | Nehlin et al. | |
| 2008/0020965 A1 | 1/2008 | Light et al. | |
| 2009/0170163 A1 | 7/2009 | Shen et al. | |
| 2009/0298760 A1 | 12/2009 | Weimer et al. | |
| 2009/0304696 A1* | 12/2009 | Lawson et al. | 424/135.1 |
| 2010/0022455 A1 | 1/2010 | Chilkoti | |
| 2011/0091543 A1 | 4/2011 | Prior et al. | |

FOREIGN PATENT DOCUMENTS

| | | |
|---|---|---|
| CN | 101177456 A | 5/2008 |
| EP | 1 816 201 A1 | 8/2007 |
| JP | 2005-508623 A | 4/2005 |
| JP | 2009-525724 A | 7/2009 |
| WO | WO 03/020746 A1 | 3/2003 |
| WO | WO 2009-158704 A2 | 12/2009 |

OTHER PUBLICATIONS

International Preliminary Report on Patentability for Application No. PCT/KR2011/004131; dated Dec. 4, 2012.
Office Action for Chinese Application No. 201180027707.6; dated Mar. 21, 2014.
Hagan, F. S., et al.; "*Characterization of a cDNA coding for human factor VII;*" Proceedings of the National Academy of Science, vol. 83, No. 8; pp. 2412-2416; dated Apr. 1986; retrieved on Sep. 20, 2013 from <http://www.pnas.org/content/83/8/2412.full.pdf+html>.
Halabian, R., et al.; "*Expression and purification of recombinant human coagulation factor VII fused to a histidine tag using Gateway technology;*" Blood Transfusion, vol. 7, No. 4; pp. 305-312; dated Oct. 2009; retrieved on Sep. 20, 2013 from <http://www.bloodtransfusion.it/articolo.aspx?idart=002102&idriv=52>.
Persson, E., et al.; "*Recombinant coagulation factor VIIa—from molecular to clinical aspects of a versatile haemostatic agent;*" Thrombosis Research, vol. 125, No. 6; pp. 483-489; dated Jun. 2010; abstract retrieved on Sep. 20, 2013 from <http://www.thrombosisresearch.com/article/S0049-3848(09)00540-4/abstract>.
Schulte, S.; "Use of albumin fusion technology to prolong the half-life of recombinant factor VIIa;" Thrombosis Research, vol. 122, Supplement 14; pp. S14-S19; dated 2008; abstract retrieved on Sep. 20, 2013 from <http://www.thrombosisresearch.com/article/S0049-3848(08)70029-X/abstract>.
International Search Report and Written Opinion for Application No. PCT/KR2011/004131; dated Feb. 6, 2012.
Kim, B.-J. et al., *Transferrin Fusion Technology: A Novel Approach to Prolonging Biological Half-Life of Insulinotropic Peptides*, the Journal of Pharmacology and Experimental Therapeutics, vol. 334, No. 3 (May 2010) 682-692.
Supplementary European Search Report for Application No. EP 11 79 0052 dated Oct. 8, 2013.
Zhao, H. L. et al., *Increasing the homogeneity, stability and activity of human serum albumin and interferon-a2b fusion protein by linker engineering*, Protein Expression and Purification, vol. 61, No. 1, (2008) 73-77.
Office Action for Japanese Application No. 2013-513120 dated Apr. 21, 2015, 7 pages.

\* cited by examiner

Fig.4
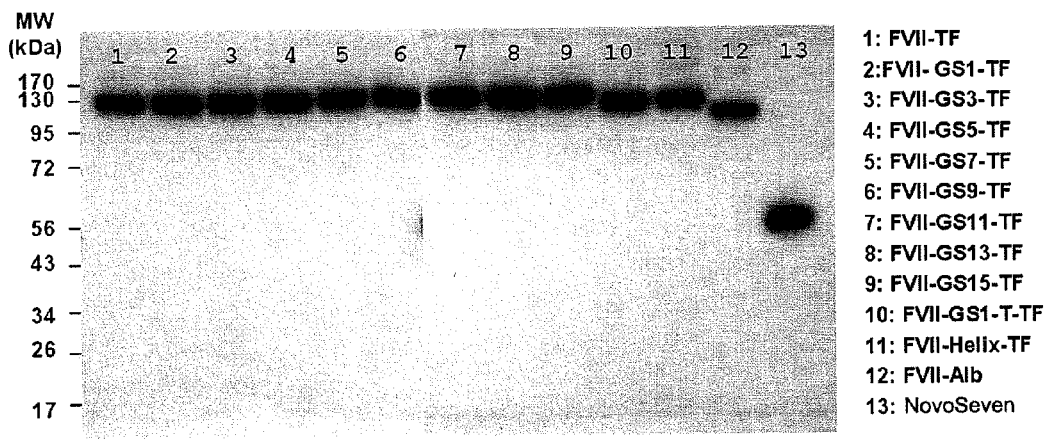
1: FVII-TF
2: FVII-GS1-TF
3: FVII-GS3-TF
4: FVII-GS5-TF
5: FVII-GS7-TF
6: FVII-GS9-TF
7: FVII-GS11-TF
8: FVII-GS13-TF
9: FVII-GS15-TF
10: FVII-GS1-T-TF
11: FVII-Helix-TF
12: FVII-Alb
13: NovoSeven
Fig.5
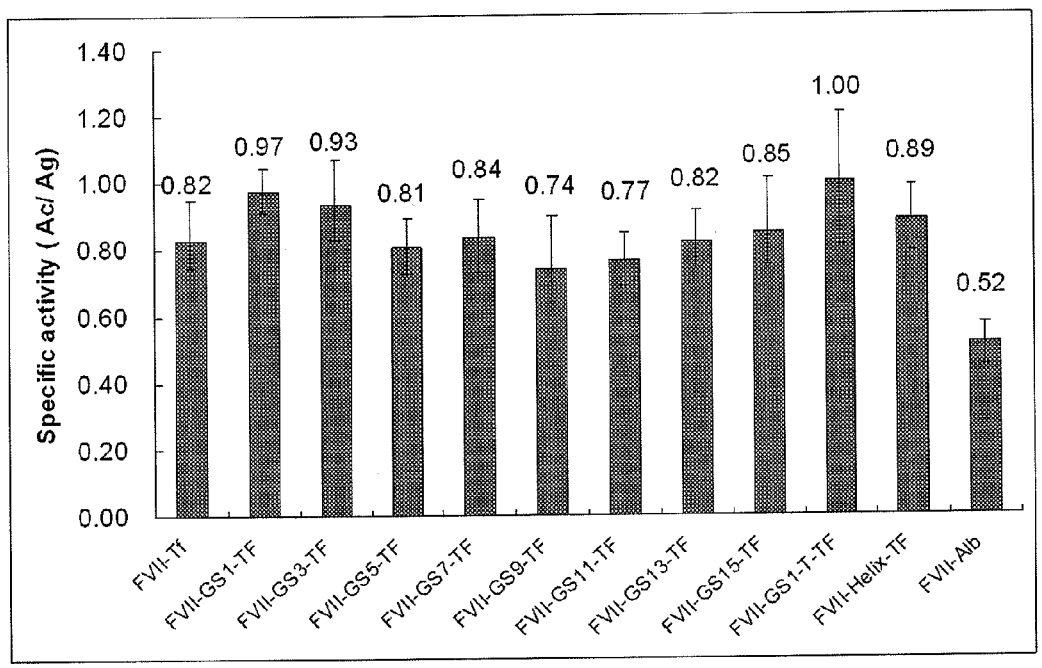
Fig.6
*Age I*
*ACC GGT* GGA GGC GGA TCC CTGGTGCCGCGCGGCAGC GGA GGC GGT TCA *ACC GGT*
Thr  Gly Gly Gly Gly Ser                                  Gly Gly Gly Ser  Thr Gly
(SEQ ID NO: 54)                                           (SEQ ID NO: 55)

1: NovoSeven
2: FVII
3: FVII-Tf
4: FVII-GS1-Tf
5: FVII-GS1-T-Tf
6: FVII-GS3-Tf
7: FVII-GS15-Tf

FUSION PROTEIN HAVING FACTOR VII ACTIVITY

TECHNICAL FIELD

The present invention relates to a fusion protein having factor VII (FVII) activity; and, more particularly, to a fusion protein comprising FVII and transferrin and having 0.7 or more of FVII specific activity compared to the unfused natural type FVII, a DNA coding therefor, a recombinant vector comprising the DNA, and a host cell comprising the recombinant vector.

BACKGROUND ART

A variety of hemorrhagic disorders are caused by the lack of blood coagulation factors. The most common disorders are hemophilia A and B caused by deficiencies or abnormality of blood coagulation factors VIII and IX, respectively.

Hemophilia A is a genetic bleeding disorder caused by an X-linked recessive trait of defective factor VIII gene. A concentrate of a plasma-derived or recombinant factor VIII has been used for the treatment of hemophilia A. Hemophilia B is caused by a deficiency or dysfunction of factor IX, which is treated by using a concentrate of plasma-derived or recombinant factor IX. However, the emergence of alloantibodies against the replacement factors remains as a serious medical problem in the treatment of hemophilia A and B. Antibodies against factor VIII are generated in up to 30% of patients with hemophilia A. Although antibodies against factor IX are less produced, they are less sensitive to an immune tolerance induction therapy, leading to more serious results.

Blood coagulation is initiated by the formation of a complex between tissue factor exposed to circulating blood after a vessel wall damage and an activated form of factor VII (FVIIa). Such complex activates factor IX and factor X and the resultant factor Xa produces the limited amount of thrombin. In a positive feedback loop, thrombin activates a variety of factors (such as factor VIII, factor V, factor XI, etc.) of blood coagulation cascade, and the activated factors constitute a factor Xase complex or a prothrombinase complex. These complexes further amplify their own generation and the production of thrombin. This sufficient amount of thrombin called 'thrombin burst' converts fibrinogen at bleeding sites to fibrin, thereby achieving complete hemostasis. However, in case of hemophilia patients having a high concentration of neutralizing antibodies against factor VIII or factor IX, no sufficient hemostasis is attained since the factor Xase complexes mentioned above can't be produced. FVIIa has been used as a major therapeutics for the patients who have neutralizing antibodies against factor VIII or factor IX, because it can activate factor X, even in the absence of factor VIII and factor IX, thereby ultimately producing a sufficient amount of thrombin to achieve the desired therapeutic effects.

FVII is a single-chain glycoprotein consisting of 406 amino acids, has a molecular weight of 50 kDa, and is secreted into blood stream as a zymogen. FVII consists of four distinct domains, i.e., an amino terminal-carboxyglutamic acid (Gla) domain, two epidermal growth factor (EGF)-like domains and a serine protease domain (Hagen F S et al., Proc. Natl. Acad. Sci. USA, 83(8):2412-2416, 1986). FVII is converted to its activated form, FVIIa, by forming two polypeptide chains linked by a disulfide bond, i.e., N-terminal light chain (24 kDa) and C-terminal heavy chain (28 kDa) through the proteolysis of a single peptide bond located at Arg152-Ile153. FVII is present at a concentration of 500 ng/mL in plasma, and 1% (i.e., 5 ng/mL) of FVII is present as FVIIa.

Meanwhile, it has been reported that the half-life of FVII in plasma is approximately 4 hours (3~6 hours), while that of FVIIa is about 2.5 hours. Due to the short half-life, FVIIa is required to be administered via multiple intravenous injections or continuous injection. However, this would limit the therapeutic uses of FVIIa in terms of high treatment expenses and making the patient's discomfort.

To overcome these problems, methods have been provided for preparing fusion proteins comprising FVII and a fusion partner linked thereto, but the resulting proteins had the problem of losing their biological activities, even though the short in-vivo half-life was somewhat improved compared to the unfused protein.

Accordingly, there are needs for providing and securing a FVII fusion protein which has an improved in-vivo half-life while retaining the biological activity of the natural type FVII.

DISCLOSURE OF INVENTION

Technical Problem

It is an object of the present invention to provide a fusion protein having the biological activity of natural type FVII.

It is other object of the present invention to provide a gene coding for the fusion protein.

It is a further object of the present invention to provide a recombinant vector comprising the gene.

It is a still further object of the present invention to provide a host cell comprising the recombinant vector.

Solution to Problem

In accordance with one aspect of the present invention, there is provided a fusion protein comprising factor VII (FVII) and transferrin, wherein the transferrin is linked to the C-terminus of the FVII.

In accordance with other aspect of the present invention, there is provided a DNA coding for the fusion protein.

In accordance with a further aspect of the present invention, there is provided a recombinant vector comprising the DNA.

In accordance with a still further aspect of the present invention, there is provided a host cell comprising the recombinant vector.

Advantageous Effects of Invention

The fusion protein according to the present invention has an improved in-vivo half-life compared to the natural type FVII while retaining a high biological activity of FVII, and thus can be effectively employed in the therapy using FVII.

BRIEF DESCRIPTION OF DRAWINGS

The above and other objects and features of the present invention will become apparent from the following description of the invention, when taken in conjunction with the accompanying drawings, which respectively show:

FIG. 4 displays Western blot results of VII-Tf, FVII-GS1-Tf, FVII-GS3-Tf, FVII-GS5-Tf, FVII-GS7-Tf, FVII-GS9-Tf, FVII-GS11-Tf, FVII-GS13-Tf, FVII-GS15-Tf, FVII-GS1-T-Tf and FVII-Helix-Tf fusion proteins of the present invention, FVII-albumin fusion protein (FVII-Alb) and FVII (NovoSeven™);

FIG. 5 is a graph showing specific activities of FVII-Tf, FVII-GS1-Tf, FVII-GS3-Tf, FVII-GS5-Tf, FVII-GS7-Tf, FVII-GS9-Tf, FVII-GS11-Tf, FVII-GS13-Tf, FVII-GS15-Tf, FVII-GS1-T-Tf and FVII-Helix-Tf fusion proteins of the present invention, and FVII-albumin fusion protein (FVII-Alb);

FIG. 6 presents the structure of a linker and restriction recognition sequences at both termini in FVII-GS1-T-Tf fusion protein (the nucleotide residues 1333-1386 of SEQ ID NO: 23)

BEST MODE FOR CARRYING OUT THE INVENTION

Figure 1:
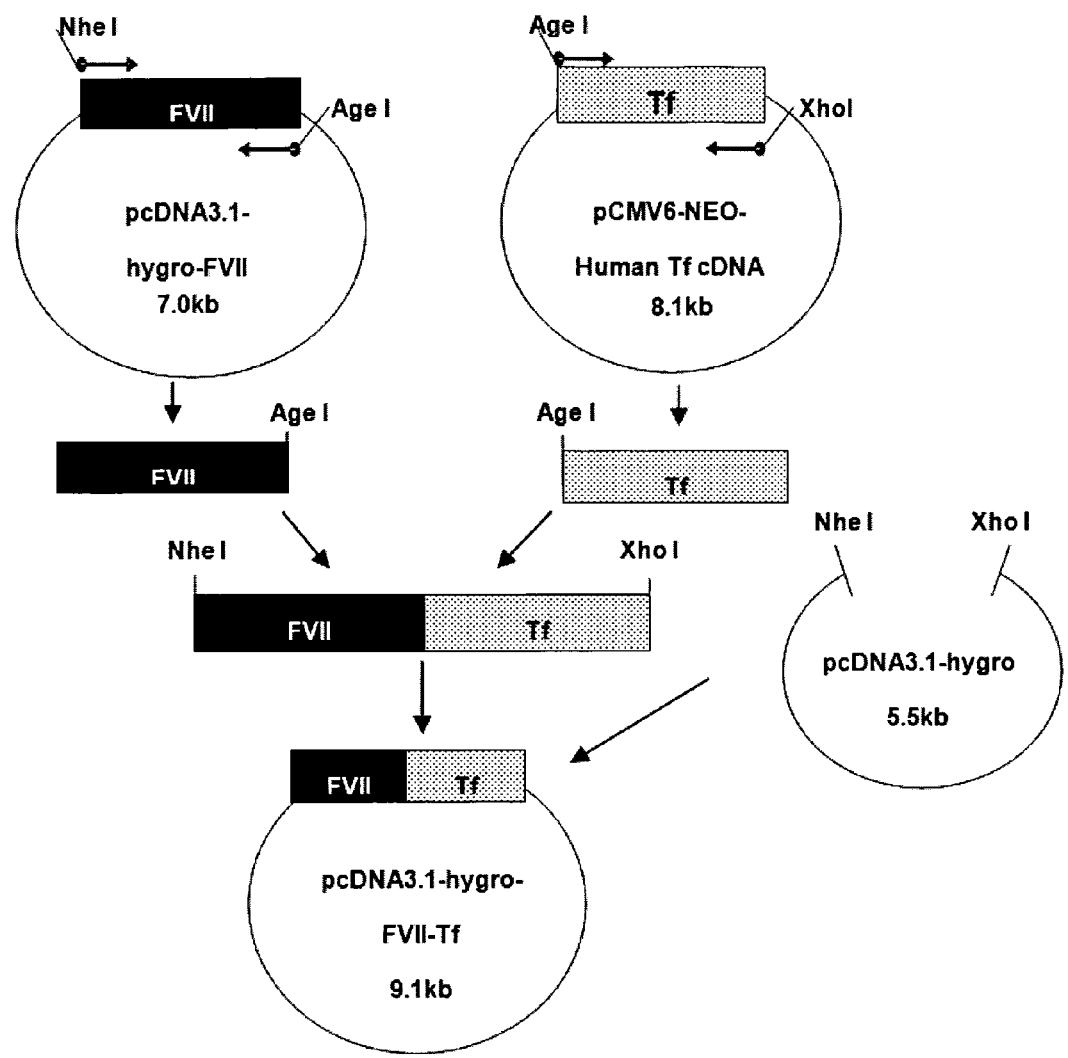
FIG. 1 is a schematic diagram showing a cloning procedure for constructing FVII-Tf expression vector from a vector comprising a cDNA coding for FVII sequence and a vector comprising a cDNA coding for transferrin (TO sequence.

The present invention provides a fusion protein comprising factor VII (FVII) and transferrin.

The FVII and transferrin of the fusion protein of the present invention may be derived from any mammal, preferably a human. More preferably, FVII and transferrin used in the present invention may have not less than 95% of sequence homologies with those of natural type of the proteins found in human blood, respectively. Most preferably, FVII has the amino acid sequence of SEQ ID NO: 1 and transferrin has the amino acid sequence of SEQ ID NO: 2.

In addition, FVII or transferrin used in the fusion protein of the present invention may be a functional equivalent or a functional derivative of natural type thereof which has a substantially equivalent functional activity. Exemplary functional equivalents include mutants induced by deletion, insertion or non-conservative or conservative substitution of any amino acid residues, or a combination thereof in amino acid sequences represented by SEQ ID NOs: 1 and 2, respectively, in which such changes do not substantially alter active sites or domains offering biological activities to FVII.

In some cases, the fusion protein of the present invention may be modified, e.g., via phosphorylation, sulfation, acrylation, glycosylation, methylation, farnesylation, acetylation, amidation, and others, for the improvement or reduction of its physical or chemical properties, and such functional derivatives also fall within the scope of the present invention so long as the biological activity of FVII is substantially retained.

In the fusion protein of the present invention, transferrin is preferably linked to the C-terminus of FVII. The fusion protein in the order of FVII-transferrin is superior to a fusion protein in the order of transferrin-FVII, probably due to the exposure of the N-terminus of the FVII (see Table 3).

The fusion protein of the present invention may further comprise recognition sequence(s) for a restriction enzyme between FVII and transferrin in order to facilitate the insertion of a linker as described below. The restriction recognition sequence may be any restriction recognition sequence known to one of ordinary skill in the art, and AgeI recognition sequence (A/CCGGT) may be preferably used. In other words, fusion proteins, in which the restriction recognition sequence is linked to the C-terminus of FVII and transferrin is linked to the restriction recognition sequence, are included within the scope of the present invention.

The present invention provides a fusion protein comprising a linker between FVII and transferrin.

The linker may have 1 to 100 amino acids, preferably 1 to 75 amino acids, more preferably 5 to 25 amino acids, and it may be any peptides which can functionally separate FVII and transferrin. The linker may have a stable secondary structure such as a helix or be originated from IgG hinge region. Preferably, the linker may rotate freely in aqueous solution and does not have a fixed structure, and, therefore, it would be non-immunogenic and would increase FVII activities of fusion proteins by minimizing the potential interference between two fusion partners. As an example, such linker may be a helix linker represented by the amino acid sequence of SEQ ID NO: 11. Further, such flexible linker may contain glycine (G) and serine (S) in a repeated or random pattern. For example, the linker comprises $(GGGGS)_N$ (SEQ ID NO: 3)$_N$ (wherein N is an integer ranging from 1 to 20), and preferably has any one selected from the group consisting of the amino acid sequences of SEQ ID NOs: 3 to 11 (see Table 1). In addition, any amino acid sequences having not less than 80% of homologies with the linker, preferably having not less than 85% of homologies may be also used in the fusion protein of the present invention.

Furthermore, the linker may also include protease cleavage site(s) which is recognized by protease(s) abundant in an injured tissue. The cleavage site may be cleaved by a protease selected from the group consisting of thrombin, factor Xa, factor IXa, and factor VIIa. The fusion protein having such protease cleavage site is cleaved at the working site to produce each protein, i.e., FVII and transferrin, and the resulting proteins function as individual proteins. Preferably, the linker has the amino acid sequence of SEQ ID NO: 12 (see Table 1).

The linker may be inserted into a fusion protein more easily via the restriction enzyme recognition sequence which is located between FVII and transferrin. Accordingly, the restriction enzyme recognition sequence may be present at any one end or both ends of the linker, and be in turn translated into amino acids encoded by the sequence. For example, when AgeI restriction enzyme recognition sequence is used, Thr may be present at the N-terminus of the linker and Thr-Gly may be present at the C-terminus of the linker. That is, when a linker (GGGGS)$_3$ (SEQ ID NO: 4) is used, The recognition sequence and linker may be present in a form of -T(GGGGS)$_3$TG-(-Thr-SEQ ID NO: 4-Thr-Gly-). The amino acids translated at the N- and C-termini of the linker may vary depending on the restriction enzyme recognition sequence employed, but the presence thereof does not influence the activities of the fusion proteins (see Table 5).

The fusion protein of the present invention exhibits not less than 0.7 of FVII specific activity compared to the unfused natural type FVII.

In an aspect of the present invention, the fusion protein, which comprises FVII represented by the amino acid sequence of SEQ ID NO: 1 and transferrin represented by the amino acid sequence of SEQ ID NO: 2, has about 0.82 to about 0.92 of FVII specific activity compared to the unfused natural type FVII (see Tables 2 and 3).

In addition, the fusion protein, which comprises FVII represented by the amino acid sequence of SEQ ID NO: 1, the linker represented by the amino acid sequence of SEQ ID NO: 3 and transferrin represented by the amino acid sequence of SEQ ID NO: 2, has about 0.97 of FVII specific activity compared to the unfused natural type FVII (see Table 2).

The fusion proteins according to the present invention, in which other linkers are inserted between FVII and transferrin, have also about 0.74 to about 1 of FVII specific activities compared to the unfused natural type FVII (see Table 2).

Furthermore, the fusion protein of the present invention has a half-life 3~4 times longer than that of FVII with no transferrin linked thereto (see Table 6).

The present invention also provides a DNA coding for the fusion protein.

The DNA coding for the fusion protein may be subjected to various changes and modifications due to the codon's degeneracy or considering codons preferred in the organism to express the fusion protein, unless the amino acid sequence of the fusion protein is substantially altered, and the modified DNAs are also included in the scope of the present invention. In the present invention, the DNA coding for the fusion protein may be preferably represented by any one of the nucleotide sequences of SEQ ID NOs: 13 to 24. The DNA coding for the fusion protein of the present invention may be provided by a vector for expressing the DNA.

The present invention provides a recombinant vector comprising the DNA coding for the fusion protein.

The term "vector" used herein refers to a means for introducing a DNA coding for said fusion protein into a host cell and expressing the fusion protein therein. The vector may include all conventional vectors such as plasmid vectors, cosmid vectors, bacteriophage vectors, virus vectors, and others, preferably a plasmid vector.

A suitable expression vector contains expression regulatory elements such as promoters, initiation codons, termination codons, polyadenylation signals and enhancers, as well as signal sequences or leader sequences for membrane targeting or secretion, and it may be diversely prepared according to the purposes. The initiation codon and termination codon should be sure to work in an organism where the gene construct is administered, and be in-frame with the coding sequence. Further, the expression vector contains a selective marker for selecting a host cell containing the vector, and an origin of replication if the expression vector is reproducible. The vector may self-replicate or be integrated into the DNA of a host cell.

Specifically, the recombinant expression vector according to the present invention may be prepared by inserting a DNA coding for the fusion protein sequence into pcDNA3.1-hygro vector.

Further, the present invention provides a host cell which produces the fusion protein by transformation with said recombinant expression vector.

Since the expression levels and modifications of the proteins vary depending on the type of host cells, it is preferred to choose a host cell most suitable for the purpose. Examples of host cells include mammal cells, e.g., Chinese hamster ovary (CHO) cells, human embryonic kidney cells (HEK293), hamster kidney cells (BHK 21), human liver cancer cells (Hep G2), and others, but not limited thereto.

In order to transform a host cell with the recombinant expression vector according to the present invention, any method known to those of ordinary skill in the art may be employed, and the example of such method includes, but not limited to, electroporation, protoplast fusion, calcium phosphate ($CaPO_4$) precipitation, calcium chloride ($CaCl_2$) precipitation, and others.

MODE FOR THE INVENTION

The following Examples are given for the purpose of illustration only, and are not intended to limit the scope of the present invention.

Example 1

Preparation of Factor VII (FVII) Plasmid Vector (pcDNA3.1-Hygro-FVII)

Total RNA purified from Hep G2 cells (KCLB No. 88065) was used as a template for reverse transcription. Complementary DNA (cDNA) transcript was amplified by PCR using FVII gene specific primers, FVII-F and FVII-R (SEQ ID NOs: 25 and 26) to obtain open reading frame of human FVII gene. The PCR was performed by treating 50 μL of reaction solution (0.5 μL of cDNA, 0.4 μM (10 pmol/μL) of primers of SEQ ID NOs: 25 and 26, 0.2 mM of dNTP, 5 unit of Taq DNA polymerase and water) under the following condition: 1 cycle of denaturation at 94° C. for 5 min, 35 cycles of amplification at 94° C. for 1 min, at 60° C. for 1 min, and at 72° C. for 2.5 min, and 1 cycle of final extension at 72° C. for 5 min. The purified PCR product was cloned into pGEM-T easy vector (Promega, Cat #: A1360). Positive clones were selected by restriction digestion using EcoRI and NcoI. The Selected clones were further verified by DNA sequencing. To transfer ORF of FVII (FVII-ORF) to an expression vector, FVII-ORF cleaved with NotI was blunted by T4 DNA polymerase and ligated with pcDNA3.1-hygro vector (Invitrogen) digested with HindIII/XbaI and blunted. The ligated vector was confirmed by restriction digestion with ApaI, XbaI, EcoRI, NcoI, PstI and DNA sequencing. This vector was designated 'pcDNA3.1-hygro-FVII'.

Example 2

Construction of FVII-Tf Expression Vector (pcDNA3.1-Hygro-FVII-Tf)

FVII cDNA prepared in Example 1 was fused to human transferrin (Tf) cDNA in order to express as a single zymogen in an animal cell. Human tranferrin cDNA was purchased from Origene (Cat #: SC322130) and was verified whether it is equal to the sequence of GenBank accession #: NM_001063.2. Primers used in the fusion were designed to remove termination codon of FVII and signal peptide of transferrin. In order to facilitate the insertion of the varying sizes of linkers between FVII and Tf, AgeI site (ACCGGT), which will be translated to threonine (Thr) and glycine (Gly), was added to the linking primers. The resulting fusion protein would have the following structure: (leader peptide)-(mature FVII)-(Thr-Gly)-(mature Tf) (in which the leader peptide consists of a signal peptide (prepeptide) not present in mature FVII and a propeptide to be cleaved by a processing enzyme, which is composed of 38 amino acids and corresponds to amino acids ranging from positions 1 to 38 in the amino acid sequence of SEQ ID NO:1). cDNAs of FVII and Tf were amplified by using primers FVII-S1, FVII-AS1, Tf-S1 and Tf-AS1 (SEQ ID NOs: 27 to 30) and the vector as described in Example 1 was used. The primers of SEQ ID NOs: 27 and 30 contains NheI and XhoI sites, respectively.

A cloning strategy for linking of FVII cDNA and Tf cDNA is depicted in FIG. 1. First, FVII cDNA was amplified from pcDNA3.1-hygro-FVII vector by PCR. The PCR was performed by treating 50 µL of reaction solution (1 µL of vector template, 1 µL of a primer set, FVII-S1 and FVII-AS1 (10 µM), 10 µL of 5× Phusion HF buffer, 200 µM of dNTP, 0.5 µL of Phusion DNA polymerase (FINNZYMES, #F-530S, 2 units/µL) and 35.5 µL of water) under the following condition: 1 cycle of denaturation at 98° C. for 30 sec, 30 cycles of amplification at 98° C. for 10 sec, at 60° C. for 45 sec, and at 72° C. for 30 sec, and 1 cycle of final extension at 72° C. for 7 min.

Next, Tf was amplified using transferrin cDNA as a template. The above mentioned PCR procedure was repeated except for using a primer set (Tf-S1: 10 µM; Tf-AS1: 10 µM).

The amplified FVII and Tf cDNA were joined by a series of restriction and ligation. Each DNA amplified by PCR was digested with AgeI and XhoI, or with NheI. The digested DNAs were purified and ligated at 1:1 molar ratio. The ligated DNA was subcloned into pcDNA3.1-hygro vector (Invitrogen) digested with NheI/XhoI. The size and sequence of insert was further verified by DNA sequencing.

Example 3

Construction of FVII-GS Linker-Tf Expression Vector

A peptide consisting of 5 amino acids comprising glycine and serine was used as a basic linker unit. The basic linker unit comprises four glycines and one serine with following sequence: 'GGGGS' (SEQ ID NO: 3). The basic linker unit (hereinafter, referred to "GS-X linker" in which X is the repeat number of the basic GS linker unit) was utilized to constitute the longer GS linkers. In this Example, the linkers ranging from GS-1 to GS-15 were constructed.

1) Construction of FVII-GS-1 Linker-Tf Expression Vector

Figure 2:
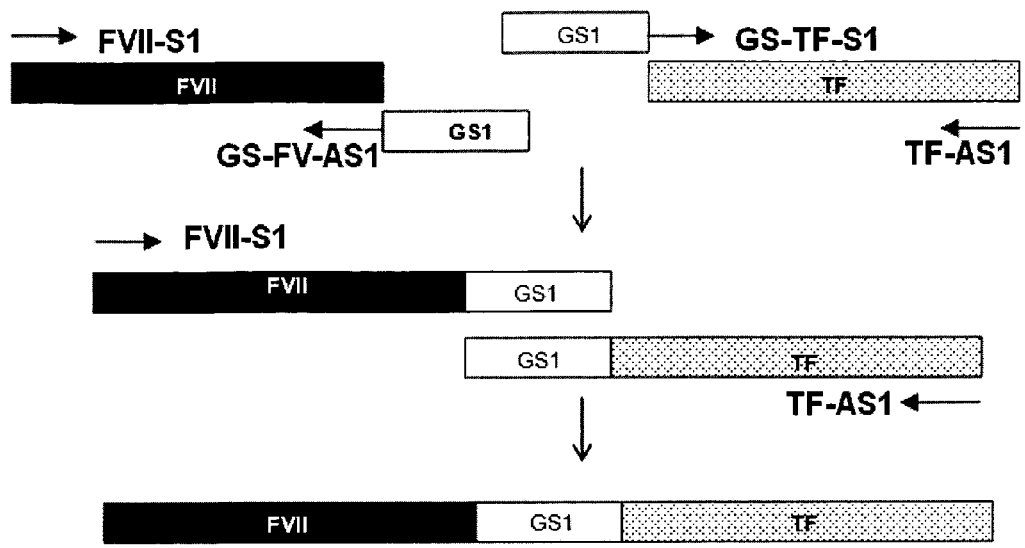
FIG. 2 is a schematic diagram showing a procedure for constructing FVII-GS1 (linker)-Tf expression vector by overlapping PCR.

A set of primers, GS-FV-AS1 and GS-Tf-S1 (SEQ ID NOs: 31 and 32), containing the basic GS linker unit was synthesized and inserted between FVII and Tf by overlapping PCR (see FIG. 2).

The GS-1 linker was linked to FVII by PCR using a set of primers FVII-S1 and GS-FV-AS1 (SEQ ID NOs: 27 and 31) and Phusion DNA polymerase (FINNZYMES, #F-530S). The PCR was performed by treating 50 µL of reaction solution (1 µL of pcDNA3.1-hygro-FVII-Tf vector, 1 µL of FVII-S1 (10 pmole/1 µL), 1 µL of GS-FV-AS1 (10 pmole/µL), 1 µL, of 10 mM dNTP, 10 µL of 5× Phusion HF buffer, 35.5 µL of water and 0.5 µL of Phusion DNA polymerase (2 unit/µL)) under the following condition: 1 cycle of denaturation at 98° C. for 30 sec, 35 cycles of amplification at 98° C. for 10 sec, at 64° C. for 30 sec, and at 72° C. for 45 sec, and 1 cycle of final extension at 72° C. for 7 min. Meanwhile, to connect the GS-1 linker to Tf, the above PCR procedure was repeated except for using a set of primers GS-Tf-S1 and Tf-AS1 (SEQ ID NOs: 32 and 30).

The amplified PCR products were utilized as overlapping PCR templates. The overlapping PCR was performed by treating the reaction solution (1 µL of amplified PCR products, 1 µL of FVII-S1 (10 pmole/µL, SEQ ID NO: 27), 1 µL of antisense primer (Tf-AS1 10 pmole/µL, SEQ ID NO: 30), 10 µL of 5× Phusion HF buffer, 1 µL of 10 mM dNTP, 34.5 µL of water, 0.5 µL of Phusion DNA polymerase (2 units/µL)) under the following condition: 1 cycle of denaturation at 98° C. for 1 min, 45 cycles of amplification at 98° C. for 10 sec, at 66/68° C. for 30 sec, and at 72° C. for 45 sec, and 1 cycle of final extension at 72° C. for 7 min. The amplified overlapping PCR product was cloned into pcDNA3.1-hygro-lacZ digested with NheI and XhoI.

2) Construction of FVII-GS-3 Linker-Tf Expression Vector

A primer set, GS3-S and GS3-AS (SEQ ID NOs: 33 and 34), containing GS-3 and AgeI site was synthesized. To make a GS-3 double stranded linker, the primers were annealed by heating a mixture (5 µL, of GS3-S (100 pmole/µL), 5 µL of GS3-AS (100 pmole/µL), 2 µL of 10× annealing buffer (100 mM Tris-Cl [pH 8.0], 1 M NaCl, 10 mM EDTA) and 8 µL of water) at 98° C. for 10 min and cooling at 25° C. for 1 hour. The annealed linker was digested with AgeI and pcDNA3.1-hygro-FVII-Tf vector prepared in Example 2 was also digested with AgeI. The digested vector was treated with 1 µL of CIP (Calf intestinal phosphatase; NEB, #M0290S) at 37° C. for 1 hour and subjected to gel extraction procedure (QIAGEN, #28704), followed by ligation at a molar ratio of 1:3 (vector:insert) using T4 DNA ligase (TAKARA, #2011A).

3) Construction of FVII-GS-5 Linker-Tf to FVII-GS-15 Linker-Tf Expression Vectors In order to construct a fusion protein expression vector containing GS-5 linker, a new strategy was implemented. FVII-Tf fusion vectors containing extended linkers were constructed by following two steps.

Figure 3:
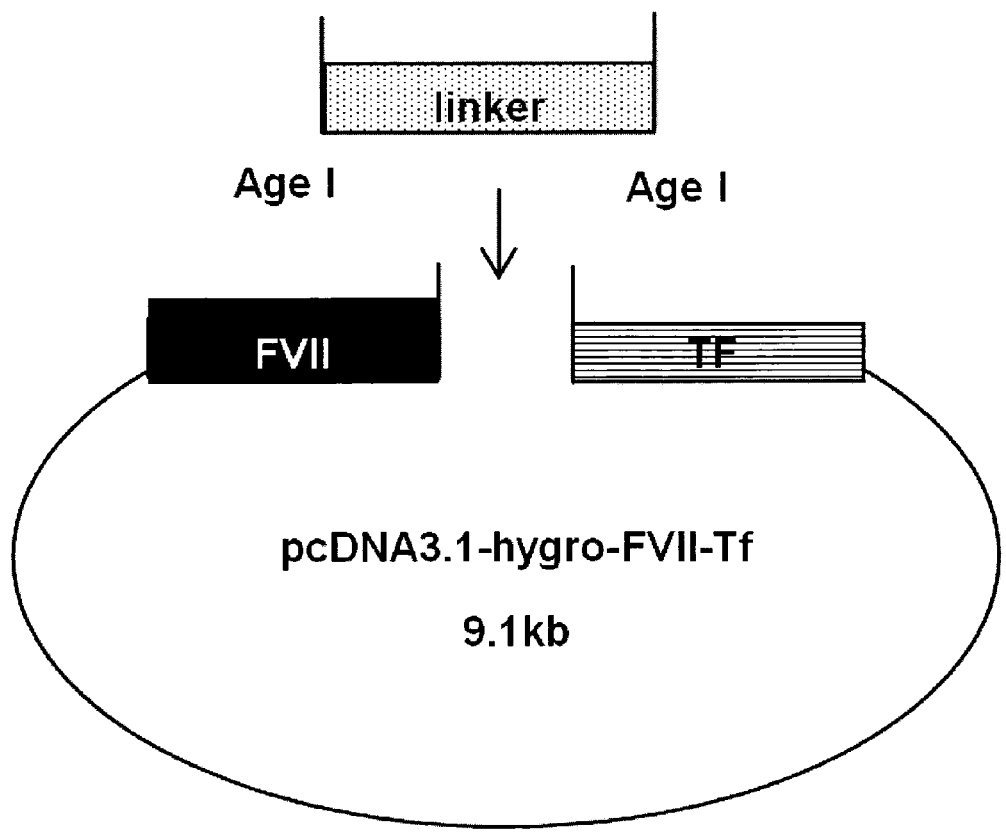
FIG. 3 is a schematic diagram showing a construction procedure of FVII-GS linker-Tf expression vectors comprising GS3, GS5, GS7, GS9, GS11, GS13, GS15 or GS-1-T as a linker.

First step is adding a synthesized double stranded (ds) GS2 linker to the previously obtained linker. After assuring the extension of linker, the linker was cut out and inserted into between FVII and Tf genes in pcDNA3.1-hygro-FVII-Tf vector. For example, to extend the GS-3 linker to GS-5 linker, the synthesized dsGS-2 linker unit of SEQ ID NO: 35 was digested with BglII and ligated with pcDNA3.1-hygro-FVII-GS3-Tf vector treated with BamHI and StuI. Next, after confirming the extension of the linker by BamH1 and AgeI digestion, the extended linker was cut out with AgeI and subcloned into pcDNA3.1-hygro-FVII-Tf vector treated with AgeI and CIP. FVII-Tf fusion expression vectors containing GS-7, GS-9, GS-11, GS-13 and GS-15 linkers were constructed by the same strategy (see FIG. 3).

Example 4

Construction of FVII-Tf Expression Vector (pcDNA3.1-Hygro-FVII-GS1-T-Tf) Containing a Linker Comprising Thrombin Cleavage Site A linker containing thrombin cleavage site was prepared by adjoining a GS-1 unit to both ends of thrombin recognition sequence (hereinafter, referred to "GS1-T linker"). dsGS1-T linker of SEQ ID NO: 36 (sense) was designed and synthesized to contain AgeI sites at both ends. The dsGS1-T linker was digested with AgeI and purified using PCR purification kit (Qiagen, cat #: 28104). The purified linker was ligated into pcDNA3.1-hygro-FVII-Tf vector treated with CTP/AgeI.

Example 5

Construction of FVII-Tf Expression Vector (pcDNA3.1-Hygro-FVII-Helix-Tf) Containing a Helix Linker A helix linker DNA was prepared by the method disclosed in U.S. Laid-open Publication No. 2009/0170163. AgeI site was added to the both ends of the prepared helix linker DNA by using primers, Helix linker S and Helix linker AS (SEQ ID NOs: 37 and 38). The primers Helix linker S and Helix linker AS were annealed and digested with AgeI, followed by insertion into pcDNA3.1-hygro-FVII-Tf vector treated with AgeI and CIP. The constructed vector was confirmed by DNA sequencing.

Comparative Example 1

Construction of FVII-Albumin Fusion Expression Vector (FVII-Alb)

The FVII-albumin fusion protein disclosed in EP Patent No. 1816201 was constructed. Human albumin cDNA was obtained by RT-PCR using human liver mRNA (Clontech) as a template and albumin gene-specific primers, Albumin-S and Albumin-AS (SEQ ID NOs: 39 and 40). RT-PCR was performed by using AccuScript High Fidelity RT-PCR system kit (Cat#600180) according to the manufacturer's manual. First, 10 μL of reverse transcription reaction solution (1 μL of 10× Reverse Transcriptase buffer, 0.6 μL of oligo-dT primer, 1 μL of dNTP, 0.4 μL of water, 5 μL of human liver mRNA (10 ng/μL)) was kept at 65° C. for 5 min and at a room temperature for 5 min, and was subjected to a reaction with 1 μL of 100 mM DTT and 1 μL of Reverse Transcriptase at 42° C. for 1 hour. A human albumin sequence was obtained by PCR using the synthesized cDNA as a template and primers Albumin-S and Albumin-AS. PCR was performed by treating 50 μL of a reaction solution (1 μL of cDNA, 10 μL of 5× Phusion HF buffer, 1 μL of primers Albumin-S and Albumin-AS, respectively, 1 μL of 10 mM dNTP, 0.5 μL of Phusion DNA polymerase (FINNZYMES, #F-530S; 2 units/μL) and 35.5 μL of water) under the following condition: 1 cycle of denaturation at 98° C. for 1 min, 30 cycles of amplification at 98° C. for 10 sec, at 62 □ for 30 sec, and at 72° C. for 60 sec, and 1 cycle of final extension at 72° C. for 7 min. The synthesized oligonucleotides of SEQ ID NOs: 41 and 42 were annealed to the GS linker [SS(GGS)$_9$GS] (SEQ ID NO: 45) disclosed in EP Patent No. 1816201. To connect the FVII cDNA prepared in Example 1 to the above linker, FVII termination codon in pcDNA3.1-hygro-FVII vector was replaced with XhoI site by PCR-based mutagenesis using primers mut FVII(XhoI)-S and mut FVII(XhoI)-AS (SEQ ID NOs: 43 and 44). Using XhoI/ApaI sites, the GS linker [SS(GGS)$_9$GS] was fused to 3' end of FVII cDNA in pcDNA3.1-hygro-FVII vector. Finally, the human albumin cDNA digested with BamHI was inserted into pcDNA3.1-hygro-FVII-GS-linker vector. The prepared pcDNA3.1-hygro-FVII-GS-linker-albumin expression vector was verified by DNA sequencing.

The characteristics of expression vectors constructed in Examples 2 to 5 and Comparative Example 1 were shown in Table 1.

TABLE 1

| FVII fusion protein | C-terminus of FVII | Linker sequence (SEQ ID NO) | N-terminus of fusion partner | Number of amino acids in linker |
|---|---|---|---|---|
| FVII-Tf | APFP (amino acid residues 441-444 of SEQ ID NO: 1) | | VPDKTV (amino acid residues 1-6 of SEQ ID NO: 2) | 0 |
| FVII-GS1-Tf | APFP | GGGGS (SEQ ID NO: 3) | VPDKTV | 5 |
| FVII-GS3-Tf | APFP | (GGGGS)$_3$ (SEQ ID NO: 4) | VPDKTV | 15 |
| FVII-GS5-Tf | APFP | (GGGGS)$_5$ (SEQ ID NO: 5) | VPDKTV | 25 |
| FVII-GS7-Tf | APFP | (GGGGS)$_7$ (SEQ ID NO: 6) | VPDKTV | 35 |
| FVII-GS9-Tf | APFP | (GGGGS)$_9$ (SEQ ID NO: 7) | VPDKTV | 45 |
| FVII-GS11-Tf | APFP | (GGGGS)$_{11}$ (SEQ ID NO: 8) | VPDKTV | 55 |
| FVII-GS13-Tf | APFP | (GGGGS)$_{13}$ (SEQ ID NO: 9) | VPDKTV | 65 |
| FVII-GS15-Tf | APFP | (GGGGS)$_{15}$ (SEQ ID NO: 10) | VPDKTV | 75 |
| FVII-GS1-T-Tf | APFP | GGGGSLVPRGSGGGS (SEQ ID NO: 12) | VPDKTV | 15 |
| FVII-Helix-Tf | APFP | GA(EAAAK)$_4$A (SEQ ID NO: 11) | VPDKTV | 23 |
| FVII-Alb | APFP | SS(GGS)$_9$GS (SEQ ID NO: 45) | DAHK | 31 |

* For FVII-Tf, Thr-Gly derived from AgeI is present.
* For the linkers of SEQ ID NOs: 4 to 12, Thr derived from AgeI is present at the N-terminus, and Thr-Gly derived from AgeI is present at the C-terminus.

Experimental Example 1

Measurement of Specific Activities of FVII-Fusion Proteins

The FVII-fusion proteins constructed in Example 2 to 5 and Comparative Example 1 were expressed in a CHO cell (CHO(VK2)) which stably expresses VKORC1 (vitamin K epoxide reductase complex subunit 1).

The expression vectors constructed in Example 2 to 5 and Comparative Example 1 were purified by using Endo-free plasmid maxi kit (Qiagen, #27104). β-galactosidase was used as an internal control for transfection. CHO (VK2) cells were seeded at a density of $1.5 \times 10^6$ cells/well in 6-well plates. The cells were incubated in α-MEM (Lonza, #12-169F) supplemented with 10% FBS (Lonza, #14-501F), 1×HT (Invitrogen, #11067-030), 4 mM L-glutamine (Lonza, #17-605E) and 200 μg/mL of hygromycin (Invitrogen, #10687-010) for 24 hours, and then transfected using lipofectamine 2000 (Invitrogen) according to the manufacturer's manual. Four hours after transfection, the medium was replaced with serum-free medium (OptiMEM), and 5 mg/mL of vitamin K was supplemented. After 48 hours of incubation, the culture medium was sampled and stored at −70° C.

FVII-fusion proteins expressed were analyzed for their chromogenic activities and antigen amounts by using COATEST factor VII assay kit (Chrmogenix, #821900-63) and FVII ELISA kit (Cedarlene Lab, #CL20030K), respectively. The assays were performed according to the manufacturer's manual. Standard human plasma normalized against WHO standard was used as a control FVII in both assays. The expression of protein was assessed via western blot analysis. Equal amounts of FVII fusion proteins were loaded based on the ELISA results. The expressed FVII-fusion proteins were found to have the expected sizes without detectable fragmentation (see FIG. 4).

Meanwhile, the specific activities of FVII-transferrin fusion proteins were 0.74 to 1, which were higher compared to that of FVII-albumin fusion protein (0.52) (see Table 2). The FVII-transferrin fusion proteins containing linkers also retained not less than 70% of FVII activities. There was no relationship between the linker lengths and the specific activities, but FVII fusion proteins with shorter GS linkers showed somewhat higher specific activities than fusion proteins with longer ones. In particular, FVII-GS1-Tf and FVII-GS1-T-Tf fusion proteins showed comparable specific activities (see FIG. 5).

TABLE 2

| FVII fusion protein | Antigen (%) | Activity (%) | Specific activity (activity/antigen) |
|---|---|---|---|
| FVII-Tf | 53.2 ± 5.0 | 43.9 ± 0.3 | 0.82 |
| FVII-GS1-Tf | 53.4 ± 3.1 | 52.0 ± 0.5 | 0.97 |
| FVII-GS3-Tf | 61.9 ± 8.0 | 57.7 ± 0.2 | 0.93 |
| FVII-GS5-Tf | 69.3 ± 5.6 | 55.9 ± 1.4 | 0.81 |
| FVII-GS7-Tf | 70.9 ± 8.2 | 59.3 ± 1.1 | 0.84 |
| FVII-GS9-Tf | 64.2 ± 8.6 | 47.5 ± 0.7 | 0.74 |
| FVII-GS11-Tf | 59.1 ± 3.9 | 45.3 ± 0.9 | 0.77 |
| FVII-GS13-Tf | 59.7 ± 5.1 | 49.1 ± 0.8 | 0.82 |
| FVII-GS15-Tf | 59.2 ± 6.0 | 50.2 ± 0.5 | 0.85 |
| FVII-GS1-T-Tf | 70.8 ± 8.7 | 71.0 ± 2.6 | 1.00 |
| FVII-Helix-Tf | 89.0 ± 5.7 | 78.9 ± 2.2 | 0.89 |
| FVII-Alb | 106.6 ± 5.4 | 54.9 ± 3.3 | 0.52 |

Example 6

Characterization of FVII Fusion Proteins According to the Direction of Tf Fusion In this Example, a fusion protein in which human transferrin (Tf) is linked to N-terminus of FVII was prepared and compared with a fusion protein in which transferrin is linked to the C-terminus of FVII, in order to examine the change of characteristics according to the direction of fusion in fusion proteins. Detailed procedure is as follows.

<6-1> Construction of Tf-FVII and Tf-GS1-T-FVII Expression Vectors

Two fusion proteins with Tf linked to N-terminus of FVII were designed as follows: (1) (leader peptide of Tf)-(mature Tf)-(Thr-Gly)-(mature FVII); and (2) (leader peptide of Tf)-(mature Tf)-(Thr)-(GS1-T; SEQ ID NO: 12)-(Thr-Gly)-(mature FWD).

First, in order to obtain a Tf gene sequence containing a leader peptide, a forward primer (Nhe-Tf: SEQ ID NO: 46) was designed to contain NheI site for the purpose of cloning and a reverse primer (Tf-Age: SEQ ID NO: 47) was designed to contain AgeI site for the purpose of removing the termination codon of transferrin and cloning. For cloning of mature FVII with leader peptide removed, a forward primer (Age-FVII: SEQ ID NO: 48) was designed to contain AgeI site and a reverse primer was designed to contain XhoI site.

For Tf gene, cDNA purchased from Origene (Cat #: SC322130) as in Example 2 was used as a PCR template. The PCR was performed by treating 50 μL of a reaction solution (1 μL of vector template, 2 μL of primers Nhe-Tf and Tf-AgeI (10 μM), 10 μL of 5× Phusion HF buffer, 1 μL of 10 mM dNTP, 0.5 μL of Phusion DNA polymerase (FINNZYMES, #F-530S, 2 units/μL) and 33.5 μL of water) under the following condition: 1 cycle of denaturation at 98° C. for 30 sec, 25 cycles of amplification at 98° C. for 10 sec, at 70° C. for 30 sec, and at 72° C. for 36 sec, and 1 cycle of final extension at 72° C. for 10 min. FVII was amplified by PCR using pcDNA3.1-hygro-FVII-GS1-T-Tf vector as a template as in Example 4. The PCR conditions were same with the above Tf PCR conditions, except for using primers Age-FVII (10 μM) and VII-Xho (10 μM).

The amplified Tf gene was inserted into pcDNA3.1-hygro-FVII-GS1-T-Tf vector by using NheI/AgeI to obtain pcDNA3.1-hygro-Tf-Tf vector. The pcDNA3.1-hygro-Tf-Tf vector and the FVII PCR product were digested with AgeI/XhoI and ligated to construct an expression vector containing pcDNA3.1-hygro-Tf-FVII fusion protein. pcDNA3.1-hygro-Tf-GS1-T-FVII expression vector was constructed by inserting the dsGS1-T sequence synthesized in Example 4 via AgeI. The constructed expression vectors were confirmed by restriction mapping and DNA sequencing.

<6-2> Expression of Fusion Proteins and Characterization

In order to characterize fusion proteins with Tf linked to the N-terminus of FVII, the expression vectors thereof, i.e., pcDNA3.1-hygro-FVII-Tf, pcDNA3.1-hygro-FVII-GS1-Tf-VII, pcDNA3.1-hygro-Tf-FVII and pcDNA3.1-hygro-Tf-GS1-T-FVII, were transiently expressed in CHO cells.

The constructed four plasmid DNAs were isolated using Endo-free maxi prep kit (Qiagen). On one day before transfection, CHO (DG44) cells cultured in T75 flasks were isolated by trypsin, and seeded at a density of $1.5 \times 10^6$ cells/well in 6-well plates. After 24 hours, the cells were transfected according to the manufacturer's manual. Four hours after transfection, the medium in each well was removed and replaced with 2 mL of a growth medium supplemented with 5 μg/mL of vitamin K. After transfection, the 6-well plate was incubated in a 37° C., 5% $CO_2$ incubator, and after 48 hours, the medium was harvested. The harvested supernatant was transferred to 1.5 mL tubes and stored −70° C. for chromogenic assay and ELISA of FVII. The plate with the medium removed was washed with 2 mL of HBSS per a well and lysed with 250 μL of a lysis solution (Tropix, #ABX210LM, 1 mM DTT addition), followed by being stored at −70° C. for β-galactosidase assay.

The chromogenic assay and FVII ELISA were performed as in Experimental Example 1. Samples for analysis were prepared by thawing the frozen-stored media following the transfection just before the experiment and obtaining the supernatant via centrifugation. Standard human plasma (Dade Behring, # ORKL13, Lot#503216F) was used as a standard in the assay.

The measurement results are shown in Table 3. For Tf-FVII and Tf-GS1-T-Tf with Tf linked to N-terminus of FVII, no activities were measured unlike FVII-Tf and FVII-GS1-T-Tf with Tf linked to the C-terminus of FVII. Further, low amounts of fusion proteins with Tf linked to N-terminus were detected in FVII ELISA. However, the fusion proteins showed similar detection sensitivities, irrespective of fusion directions, in western blot results using polyclonal antibodies of Tf. The results indicate that, when Tf is linked to N-terminus of FVII, fusion proteins with no FVII activities were generated, even though translations of amino acids were normally conducted.

TABLE 3

| Fusion protein | FVII activity (%) | FVII antigen (%) | Specific activity (activity/antigen) |
|---|---|---|---|
| FVII-Tf | 33.8 ± 0.73 | 37.0 ± 2.17 | 0.92 |
| Tf-FVII | not detected | 8.0 ± 1.51 | — |
| FVII-GS-1-T-Tf | 46.6 ± 0.29 | 43.0 ± 4.75 | 1.08 |
| Tf-GS-1-T-Tf | not detected | 13.5 ± 1.01 | — |

Example 7

Characterization of Fusion Proteins According to the Deletion of Restriction Enzyme Recognition Sequence Used in the Fusion In Example 2, restriction enzyme (AgeI) recognition sequences were used to facilitate the insertion of various linkers between FVII and Tf. As a consequence, some fusion proteins became to have Thr and Gly which are encoded by above restriction enzyme, at both ends of the linkers. In this Example, it was examined whether the properties of fusion proteins are altered or not by the presence of the restriction enzyme (AgeI) recognition sequence.

The restriction enzyme recognition sequences were deleted from FVII-GS1-T-Tf fusion protein containing GS1-T linker, by PCR-based site-directed mutagenesis using mutagenic primers. As shown in FIG. 6, this experiment was designed to delete "Thr" at the N-terminus and "Thr-Gly" at the C-terminus and primers used in the experiment are listed in Table 4.

TABLE 4

| Primer | Sequence (5'→3') | SEQ ID NO |
|---|---|---|
| TG del-S | CAG CGG AGG CGG TTC AGT CCC TGA TAA AAC TG | 50 |
| TG del-AS | CAG TTT TAT CAG GGA CTG AAC CGC CTC CGC TG | 51 |
| T del-S | CGA GCC CCA TTT CCC GGT GGA GGC GGA TC | 52 |
| T del-AS | GAT CCG CCT CCA CCG GGA AAT GGG GCT CG | 53 |

<7-1> Deletion of Thr-Gly

PCR-based mutagenesis was conducted. The PCR was performed by treating a reaction solution (1 μL of pcDNA3.1-hygro-FVII-GS1-T-Tf vector, 0.2 μL of sense primer (TG del-S10 μM), 0.2 μL of antisense primer (TG del-AS10 μM), 1 μL of 10 mM dNTP, 4 μL of 5×PCR buffer, 14 μL of water, and 0.2 μL of Phusion DNA polymerase (FINNZYMES, #F-530S)) under the following condition: 1 cycle of denaturation at 98° C. for 30 sec, 18 cycles of amplification at 98° C. for 10 sec, at 58° C. for 30 sec, and at 72° C. for 3 min, and 1 cycle of final extension at 72° C. for 7 min. In order to remove the original template DNA, the amplified PCR product was treated with 1 μL of DpnI (NEB, #R0176S) and incubated at 37° C. for 1 hour. 50 μL of HIT competent cell (DH5α, RH617) was transformed using 10 μL of the DpnI-treated DNA and incubated in at an LB+amp (10 mg/mL) solid medium overnight. Four clones thus obtained were analyzed by DNA sequencing and two clones were verified as mutants.

<7-2> Deletion of Thr

In order to delete Thr, the similar method as in Example <7-1> was conducted by using different primers. Briefly, PCR-based mutagenesis was performed by using, as a template, 1 μL of plasmid DNA of the clones in which the mutation was confirmed in Example <7-1> and 1 μL of sense primer (T del-S; 10 pmole) and 1 μL of antisense primer (T del-AS; 10 pmole), under the same condition. By DNA sequencing of four clones which were selected, three clones were confirmed to have mutations. The secured expression vector was named "pcDNA3.1-hygro-FVII-GS1-T-Tf(M3)".

<7-3> Characterization of Fusion Proteins with Restriction Enzyme Recognition Sequences Deleted CHO cells were transfected with FVII-GS1-T-Tf and FVII-GS1-T-Tf(M3) expression vectors and FVII-Alb expression vector as a control, and the supernatants of the media were obtained. The obtained supernatants were subjected to FVII chromogenic assay (Chromogenix) and FVII ELISA (cedarlane) to verify the change in the ratio of activity/antigen. As shown in Table 5, the antigen amounts and activities of FVII-GS1-T-Tf and FVII-GS1-T-Tf(M3) fusion proteins were almost equal each other, and the ratios (specific activities) also did not vary. In addition, the specific activities were confirmed to be significantly higher than that of FVII-Alb fusion protein.

TABLE 5

|  | FVII antigen (%) | FVII activity (%) | Specific activity (activity/antigen) |
|---|---|---|---|
| FVII-GS1-T-Tf | 34.1 ± 2.1 | 39.6 ± 2.2 | 1.16 |
| FVII-GS1-T-Tf(M3) | 33.5 ± 4.7 | 38.0 ± 0.7 | 1.14 |
| FVII-Alb | 50.1 ± 1.2 | 26.3 ± 0.8 | 0.53 |

Example 8

Measurement of Half-Life of Fusion Proteins

In order to examine the increase of half-life in the fusion proteins according to the present invention, FVII-Tf, FVII-GS1-Tf, FVII-GS3-Tf, FVII-GS15-Tf and FVII-GS1-T-Tf were used as experimental groups, and a wild type FVII and commercially available FVIIa (NovoSeven®; Novo Nordisk) were used as control groups.

<8-1> Sample Preparation

1) Securing Expression Medium

Wild type FVII protein and five Tf-fused FVII fusion proteins were expressed in FreeStyle™ CHO-S cell line (Invitrogen, Cat. no. R800-07). The CHO-S cells were cultured in suspension in a spinner flask with freestyle CHO expression medium supplemented with 8 mM L-glu (GIBCO, L-glutamine 200 mM (100×), Cat. No. 25030-081). The cultured cells were seeded at a density of $4 \times 10^5$ cells/mL before 24 hours to transfection, and were transfected when the density becomes $1 \times 10^6$ cells/mL. The DNAs used in the transfection were prepared by using Endo-free maxi prep kit (QIAGEN, Cat. No. 12362) or Endo-free plasmid mega prep kit (QIAGEN, 12381), and the transfection was conducted in reference to the transfection protocol of FreeStyle MAX Reagent (Invitrogen, Cat. No. 16447-100). 500 µg of DNA was added to 8 mL of OptiPRO SFM (Invitrogen, Cat. No. 12309-019) and mixed. To another tube, 8 mL of OptiPRO SFM (Invitrogen, Cat. No. 12309-019) and 500 µL, of FreeStyle Max Reagent was added, and then the above two mixture was slowly mixed and stored at room temperature for 10 min. After 10 min, FreeStyle™ CHO-S cells were transfected with the mixture. The transfected cells were cultured in a 37° C., 5% $CO_2$ incubator for 3~5 days, and then the supernatant was obtained.

2) Purification of Expression Medium

The medium obtained by a spinner flask culture was filtered through 0.22 µm of filter (Corning) to remove remaining cells and debris. The filtered medium was concentrated 10-fold by ultrafiltration using tangential-flow membrane (satorious, 30 KDa). The concentrated medium was applied to an XK16/20 column (GE healthcare) charged with Ceramic Hydroxyapatite (BIO-RAD, 157-0040) resin. The Ceramic Hydroxyapatite column was equilibrated with more than 10 column volume of equilibration buffer (25 mM imidazole, 0.02% Tween 80 and 150 mM NaCl, pH 6.5). After the concentrated medium was loaded, the column was washed with the equilibration buffer and wash buffer-1 (25 mM imidazole, 0.02% Tween 80, 100 mM sodium phosphate, pH 6.3) and wash buffer-2 (25 mM imidazole, 0.02% Tween 80, 100 mM sodium phosphate, 1M NaCl, pH 6.3).

After washing, the fusion protein captured to the column was eluted with an elution buffer (25 mM imidazole, 0.02% Tween 80, 500 mM sodium phosphate, pH 6.3). The eluted protein was analyzed by FVII-chromogenic assay, FVII ELISA assay and SDS-PAGE/western blot.

<8-2> Western Blot Assay

FVII and FVII/Tf fusion proteins partially purified via two-step columns were confirmed to have 45% or more of purities by SDS-PAGE/Coomassie Blue staining. The presence of FVII-derived fragments in the purified proteins was assessed by western blot, since the fragmented FVIIs in purified fusion proteins might have shorter half-life than intact FVII fusion protein and mislead the determination of half-life of each FVII fusion protein. NovoSeven®(Novo Nordisk, 1.2 mg/vial, 60 KIU) and the purified samples were prepared at 0.1 IU (FVII activity)/10 µL, and then SDS-PAGE was conducted by using NuPage 4-12% bis-Tri gel (Invitrogen). After the completion of electrophoresis, the gel was transferred to a PVDF membrane and the membrane was blocked at room temperature for 1 hour by adding 10 mL of blocking buffer (25 mM Tris, 150 mM NaCl (pH 7.2), 5% skin milk and 0.1% Tween 80). The blocking solution was decanted, and 10 mL (5% skim milk in PBS-T) of anti-FVII antibody (Cat. No. F8146, Sigma) or mouse anti-transferrin antibody (sc52256, santa cruz) was added at a ratio of 1:5000 and 1:500, and incubated for 1 hour in a rocking shaker. The membrane was washed four times with a washing solution (25 mM Tris, 150 mM NaCl, pH 7.2) and incubated for 1 hour in 10 mL (5% skim milk in PBS-T) of solution in which goat anti-mouse IgG-BRP antibody (Cat. No. G21040, Invitrogen) as a secondary antibody has been added at a ratio of 1:50,000. After the membrane was washed four times with a wash solution (25 mM Tris, 150 mM NaCl, pH 7.2), 2 ml of Super-signal west Femto mix (Thermo) was added onto it for 5 min. After the completion of the reaction, the film was developed.

Figure 7:
FIG. 7 shows western blot results of purified FVII-Tf, FVII-GS1-Tf, FVII-GS1-T-Tf, FVII-GS3-Tf, and FVII-GS15-Tf fusion proteins of the present invention, NovoSeven™ and FVII.

The western blot results were shown in FIG. 7. As shown in FIG. 7, no FVII-derived fragments were detected in the purified proteins. No fragmented transferrins were detected on the blot probed by anti-transferrin antibody.

<8-3> Measurement of Half-Life

The half-lives of the fusion protein having no linker, the fusion proteins having four linkers (GS1, GS1-T, GS3 and GS15), and a wild type FVII expressed and purified under the same condition and a commercially available Novo-Seven as controls were measured and compared each other in rats. The quantitative analysis of FVII amount in samples to be administered and samples collected from animal experiment was conducted by human FVII ELISA (Cedarlane, Paired Antibodies for ELISA factor VII, #CL20030K), according to the manufacturer's instruction. The concentrations of samples to be administered were determined by averaging the values from three different dilutions of a sample. Administration dilution solution (NaCl 3 mg/mL, $CaCl_2$ dihydrate 1.5 mg/mL, glycylglycine 1.3 mg/mL, polysorbate 80 0.1 mg/mL and mannitol 30 mg/mL, pH 5.5) was used as a diluent. After FVII ELISA quantification, each protein was diluted with the administration dilution solution, and the diluted sample was intravenously administered to rats (250-300 g of Sprague Dawley, three rats per group) via tail vein at 150 IU/kg based on the weights of rats measured on the day of experiment. The bloods were taken at total eleven time points, i.e., 0 min, 5 min, 15 min, 30 min, 60 min, 1.5 hour, 2 hour, 4 hour, 6 hour, 8 hour and 24 hour after administration of the drug. 225 μL of the blood and 25 μL of 3.2% sodium citrate were mixed and centrifuged at 4° C. and 13,000 rpm for 1 min, followed by storing the supernatant at −70° C. Rat plasma was analyzed by dilution of 1/50 or 1/100 with a wash buffer used in FVII ELISA kit (cedarlane). Regression curve was obtained by plotting logarithm of human FVII antigen concentration versus the time points of sampling. The half-life of each FVII was determined by calculating from the formula 'half-life=ln 2/slope of regression curve'. As shown in Table 6, the fusion proteins of the present invention showed 3~4 folds of improved half-life compared to wild type FVII.

TABLE 6

| Type | Half-life (min) |
|---|---|
| FVII-GS1-Tf | 254.2 ± 19.1 |
| FVII-GS3-Tf | 227.4 ± 23.5 |
| FVII-GS1-T-Tf | 235.4 ± 27.4 |
| FVII-GS15-Tf | 257.0 ± 23.9 |
| FVII-Tf | 277.0 ± 24.5 |
| NovoSeven | 80.3 ± 27.4 |
| Natural type FVII | 59.6 ± 2.9 |

The invention claimed is:

1. A fusion protein comprising factor VII (FVII) and transferrin, wherein said transferrin is linked to the C-terminus of said FVII, and which further comprises a linker between the FVII and the transferrin, and one or more amino acids translated from a restriction enzyme recognition sequence between said C-terminus of said FVII and said transferrin; and wherein the linker comprises a protease cleavage site, which is capable of being cleaved by a protease selected from the group consisting of thrombin, factor Xa, factor IXa, and factor VIIa.

2. The fusion protein of claim 1, wherein said FVII is a polypeptide represented by the amino acid sequence of SEQ ID NO: 1.

3. The fusion protein of claim 1, wherein said transferrin is a polypeptide represented by the amino acid sequence of SEQ ID NO: 2.

4. The fusion protein of claim 1, wherein the linker consists of 1 to 100 amino acids.

5. The fusion protein of claim 1, wherein the linker consists of 1 to 75 amino acids.

6. The fusion protein of claim 1, wherein the linker consists of 5 to 25 amino acids.

7. The fusion protein of claim 1, wherein one or more amino acids translated from the restriction enzyme recognition site are present at one end or both ends of the linker.

8. The fusion protein of claim 1, wherein the linker is a peptide represented by any one of the amino acid sequences of SEQ ID NOs: 3 to 11.

* * * * *

SEQUENCE LISTING

```
<160> NUMBER OF SEQ ID NOS: 56

<210> SEQ ID NO 1
<211> LENGTH: 444
<212> TYPE: PRT
<213> ORGANISM: Homo sapiens
<220> FEATURE:
<221> NAME/KEY: PEPTIDE
<222> LOCATION: (1)...(444)
<223> OTHER INFORMATION: Factor VII protein

<400> SEQUENCE: 1

Met Val Ser Gln Ala Leu Arg Leu Leu Cys Leu Leu Leu Gly Leu Gln
 1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255
```

```
Asp Glu Gln Ser Arg Arg Val Ala Gln Val Ile Ile Pro Ser Thr Tyr
              260                 265                 270

Val Pro Gly Thr Thr Asn His Asp Ile Ala Leu Leu Arg Leu His Gln
          275                 280                 285

Pro Val Val Leu Thr Asp His Val Val Pro Leu Cys Leu Pro Glu Arg
      290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
              325                 330                 335

Val Leu Asn Val Pro Arg Leu Met Thr Gln Asp Cys Leu Gln Gln Ser
          340                 345                 350

Arg Lys Val Gly Asp Ser Pro Asn Ile Thr Glu Tyr Met Phe Cys Ala
      355                 360                 365

Gly Tyr Ser Asp Gly Ser Lys Asp Ser Cys Lys Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
              405                 410                 415

Arg Val Ser Gln Tyr Ile Glu Trp Leu Gln Lys Leu Met Arg Ser Glu
          420                 425                 430

Pro Arg Pro Gly Val Leu Leu Arg Ala Pro Phe Pro
      435                 440

<210> SEQ ID NO 2
<211> LENGTH: 679
<212> TYPE: PRT
<213> ORGANISM: Homo sapiens
<220> FEATURE:
<221> NAME/KEY: PEPTIDE
<222> LOCATION: (1)...(679)
<223> OTHER INFORMATION: Transferrin protein

<400> SEQUENCE: 2

Val Pro Asp Lys Thr Val Arg Trp Cys Ala Val Ser Glu His Glu Ala
 1               5                  10                  15

Thr Lys Cys Gln Ser Phe Arg Asp His Met Lys Ser Val Ile Pro Ser
              20                  25                  30

Asp Gly Pro Ser Val Ala Cys Val Lys Lys Ala Ser Tyr Leu Asp Cys
          35                  40                  45

Ile Arg Ala Ile Ala Ala Asn Glu Ala Asp Ala Val Thr Leu Asp Ala
      50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
              85                  90                  95

Ala Val Ala Val Val Lys Lys Asp Ser Gly Phe Gln Met Asn Gln Leu
          100                 105                 110

Arg Gly Lys Lys Ser Cys His Thr Gly Leu Gly Arg Ser Ala Gly Trp
      115                 120                 125

Asn Ile Pro Ile Gly Leu Leu Tyr Cys Asp Leu Pro Glu Pro Arg Lys
      130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
```

-continued

```
                165                 170                 175
Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
    370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
        435                 440                 445

Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
            580                 585                 590
```

-continued

```
Lys Glu Ala Cys Val His Lys Ile Leu Arg Gln Gln His Leu Phe
            595                 600                 605
Gly Ser Asn Val Thr Asp Cys Ser Gly Asn Phe Cys Leu Phe Arg Ser
        610                 615                 620
Glu Thr Lys Asp Leu Leu Phe Arg Asp Asp Thr Val Cys Leu Ala Lys
625                 630                 635                 640
Leu His Asp Arg Asn Thr Tyr Glu Lys Tyr Leu Gly Glu Glu Tyr Val
                645                 650                 655
Lys Ala Val Gly Asn Leu Arg Lys Cys Ser Thr Ser Leu Leu Glu
            660                 665                 670
Ala Cys Thr Phe Arg Arg Pro
        675

<210> SEQ ID NO 3
<211> LENGTH: 5
<212> TYPE: PRT
<213> ORGANISM: Artificial Sequence
<220> FEATURE:
<223> OTHER INFORMATION: Linker GS-1
<220> FEATURE:
<223> OTHER INFORMATION: Synthesized

<400> SEQUENCE: 3

Gly Gly Gly Gly Ser
1               5

<210> SEQ ID NO 4
<211> LENGTH: 15
<212> TYPE: PRT
<213> ORGANISM: Artificial Sequence
<220> FEATURE:
<223> OTHER INFORMATION: Linker GS-3
<220> FEATURE:
<223> OTHER INFORMATION: Synthesized

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 25
<212> TYPE: PRT
<213> ORGANISM: Artificial Sequence
<220> FEATURE:
<223> OTHER INFORMATION: Linker GS-5
<220> FEATURE:
<223> OTHER INFORMATION: Synthesized

<400> SEQUENCE: 5

Gly Gly Gly Gly Ser Gly Gly Gly Gly Ser Gly Gly Gly Gly Ser Gly
1               5                   10                  15
Gly Gly Ser Gly Gly Gly Gly Ser
            20                  25

<210> SEQ ID NO 6
<211> LENGTH: 35
<212> TYPE: PRT
<213> ORGANISM: Artificial Sequence
<220> FEATURE:
<223> OTHER INFORMATION: Linker GS-7
<220> FEATURE:
<223> OTHER INFORMATION: Synthesized

<400> SEQUENCE: 6
```

```
Gly Gly Gly Gly Ser Gly Gly Gly Gly Ser Gly Gly Gly Gly Ser Gly
  1               5                  10                  15

Gly Gly Gly Ser Gly Gly Gly Gly Ser Gly Gly Gly Ser Gly Gly
            20                  25                  30

Gly Gly Ser
        35
```

<210> SEQ ID NO 7
<211> LENGTH: 45
<212> TYPE: PRT
<213> ORGANISM: Artificial Sequence
<220> FEATURE:
<223> OTHER INFORMATION: Linker GS-9
<220> FEATURE:
<223> OTHER INFORMATION: Synthesized

<400> SEQUENCE: 7

```
Gly Gly Gly Gly Ser Gly Gly Gly Gly Ser Gly Gly Gly Gly Ser Gly
  1               5                  10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45
```

<210> SEQ ID NO 8
<211> LENGTH: 55
<212> TYPE: PRT
<213> ORGANISM: Artificial Sequence
<220> FEATURE:
<223> OTHER INFORMATION: Linker GS-11
<220> FEATURE:
<223> OTHER INFORMATION: Synthesized

<400> SEQUENCE: 8

```
Gly Gly Gly Gly Ser Gly Gly Gly Gly Ser Gly Gly Gly Gly Ser Gly
  1               5                  10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55
```

<210> SEQ ID NO 9
<211> LENGTH: 65
<212> TYPE: PRT
<213> ORGANISM: Artificial Sequence
<220> FEATURE:
<223> OTHER INFORMATION: Linker GS-13
<220> FEATURE:
<223> OTHER INFORMATION: Synthesized

<400> SEQUENCE: 9

```
Gly Gly Gly Gly Ser Gly Gly Gly Gly Ser Gly Gly Gly Gly Ser Gly
  1               5                  10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser
```

<210> SEQ ID NO 10
<211> LENGTH: 75
<212> TYPE: PRT
<213> ORGANISM: Artificial Sequence
<220> FEATURE:
<223> OTHER INFORMATION: Linker GS-15
<220> FEATURE:
<223> OTHER INFORMATION: Synthesized

<400> SEQUENCE: 10

```
Gly Gly Gly Gly Ser Gly Gly Gly Ser Gly Gly Gly Gly Ser Gly
1               5                   10                  15
Gly Gly Gly Ser Gly Gly Gly Gly Ser Gly Gly Gly Gly Ser Gly
                20                  25                  30
Gly Gly Ser Gly Gly Gly Gly Ser Gly Gly Gly Gly Ser Gly Gly
            35                  40                  45
Gly Ser Gly Gly Gly Ser Gly Gly Gly Ser Gly Gly Gly Gly
    50                  55                  60
Ser Gly Gly Gly Gly Ser Gly Gly Gly Ser
65                  70                  75
```

<210> SEQ ID NO 11
<211> LENGTH: 23
<212> TYPE: PRT
<213> ORGANISM: Artificial Sequence
<220> FEATURE:
<223> OTHER INFORMATION: Linker Helix
<220> FEATURE:
<223> OTHER INFORMATION: Synthesized

<400> SEQUENCE: 11

```
Gly Ala Glu Ala Ala Ala Lys Glu Ala Ala Lys Glu Ala Ala Ala
1               5                   10                  15
Lys Glu Ala Ala Ala Lys Ala
                20
```

<210> SEQ ID NO 12
<211> LENGTH: 15
<212> TYPE: PRT
<213> ORGANISM: Artificial Sequence
<220> FEATURE:
<223> OTHER INFORMATION: Linker GS1-T
<220> FEATURE:
<223> OTHER INFORMATION: Synthesized

<400> SEQUENCE: 12

```
Gly Gly Gly Gly Ser Leu Val Pro Arg Gly Ser Gly Gly Gly Ser
1               5                   10                  15
```

<210> SEQ ID NO 13
<211> LENGTH: 3378
<212> TYPE: DNA
<213> ORGANISM: Artificial Sequence
<220> FEATURE:
<223> OTHER INFORMATION: gene sequence encoding FVII-Tf protein
<220> FEATURE:
<223> OTHER INFORMATION: Synthesized

<400> SEQUENCE: 13

```
atggtctccc aggccctcag gctcctctgc cttctgcttg ggcttcaggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
```

```
tccttcgagg aggcccggga gatcttcaag gacgcggaga ggacgaagct gttctggatt      240
tcttacagtg atggggacca gtgtgcctca agtccatgcc agaatggggg ctcctgcaag      300
gaccagctcc agtcctatat ctgcttctgc ctccctgcct tcgagggccg gaactgtgag      360
acgcacaagg atgaccagct gatctgtgtg aacgagaacg gcggctgtga gcagtactgc      420
agtgaccaca cgggcaccaa gcgctcctgt cggtgccacg aggggtactc tctgctggca      480 gacgggtgt cctgcacacc cacagttgaa tatccatgtg gaaaaatacc tattctagaa       540 aaagaaatg ccagcaaacc ccaaggccga attgtggggg gcaaggtgtg ccccaaaggg       600
gagtgtccat ggcaggtcct gttgttgtg aatggagctc agttgtgtgg ggggaccctg       660
atcaacacca tctgggtggt ctccgcggcc cactgtttcg acaaaatcaa gaactggagg      720
aacctgatcg cggtgctggg cgagcacgac ctcagcgagc acgacgggga tgagcagagc      780
cggcgggtgg cgcaggtcat catccccagc acgtacgtcc cgggcaccac caaccacgac      840
atcgcgctgc tccgcctgca ccagcccgtg gtcctcactg accatgtggt gcccctctgc      900
ctgcccgaac ggacgttctc tgagaggacg ctggccttcg tgcgcttctc attggtcagc      960
ggctggggcc agctgctgga ccgtggcgcc acggccctgg agctcatggt cctcaacgtg     1020
ccccggctga tgacccagga ctgcctgcag cagtcacgga aggtgggaga ctccccaaat     1080
atcacggagt acatgttctg tgccggctac tcggatggca gcaaggactc ctgcaagggg     1140
gacagtggag gccacatgc cacccactac cggggcacgt ggtacctgac gggcatcgtc      1200
agctggggcc agggctgcgc aaccgtgggc cactttgggg tgtacaccag gtctcccag     1260 tacatcgagt ggctgcaaaa gctcatgcgc tcagagccac gcccaggagt cctcctgcga     1320 gcccattc ccaccggtgt ccctgataaa actgtgagat ggtgtgcagt gtcggagcat       1380
gaggccacta agtgccagag tttccgcgac catatgaaaa gcgtcattcc atccgatggt     1440
cccagtgttg cttgtgtgaa gaaagcctcc taccttgatt gcatcagggc cattgcggca     1500
aacgaagcgg atgctgtgac actggatgca ggtttggtgt atgatgctta cctggctccc     1560
aataacctga gcctgtggt ggcagagttc tatgggtcaa agaggatcc acagactttc       1620 tattatgctg ttgctgtggt gaagaaggat agtggcttcc agatgaacca gcttcgaggc     1680
aagaagtcct gccacacggg tctaggcagg tccgctgggt ggaacatccc cataggctta     1740
ctttactgtg acttacctga gccacgtaaa cctcttgaga aagcagtggc caatttcttc     1800
tcgggcagct gtgcccctg tgcggatggg acggacttcc cccagctgtg tcaactgtgt     1860
ccagggtgtg gctgctccac ccttaaccaa tacttcggct actcaggagc cttcaagtgt     1920
ctgaaggatg gtgctgggga tgtggccttt gtcaagcact cgactatatt tgagaacttg     1980
gcaaacaagg ctgacaggga ccagtatgag ctgctttgcc tggacaacac ccggaagccg     2040
gtagatgaat acaaggactg ccacttggcc caggtcccttt ctcataccgt cgtggcccga    2100
agtatgggcg gcaaggagga cttgatctgg gagcttctca accaggccca ggaacatttt    2160
ggcaaagaca aatcaaaaga attccaacta ttcagctctc ctcatgggaa ggacctgctg    2220
tttaaggact ctgcccacgg gtttttaaaa gtccccccca ggatggatgc caagatgtac    2280
ctgggctatg agtatgtcac tgccatccgg aatctacggg aaggcacatg cccagaagcc    2340
ccaacagatg aatgcaagcc tgtgaagtgg tgtgcgctga gccaccacga gaggctcaag    2400
tgtgatgagt ggagtgttaa cagtgtaggg aaaatagagt gtgtatcagc agagaccacc    2460
gaagactgca tcgccaagat catgaatgga gaagctgatg ccatgagctt ggatggaggg    2520
```

-continued

| | |
|---|---|
| tttgtctaca tagcgggcaa gtgtggtctg gtgcctgtct tggcagaaaa ctacaataag | 2580 |
| agcgataatt gtgaggatac accagaggca gggtattttg ctgtagcagt ggtgaagaaa | 2640 |
| tcagcttctg acctcacctg ggacaatctg aaaggcaaga agtcctgcca tacggcagtt | 2700 |
| ggcagaaccg ctggctggaa catccccatg ggcctgctct acaataagat caaccactgc | 2760 |
| agatttgatg aattttcag tgaaggttgt gcccctgggt ctaagaaaga ctccagtctc | 2820 |
| tgtaagctgt gtatgggctc aggcctaaac ctgtgtgaac ccaacaacaa agagggatac | 2880 |
| tacggctaca caggcgcttt caggtgtctg gttgagaagg agatgtggc ctttgtgaaa | 2940 |
| caccagactg tcccacagaa cactgggga aaaaacctg atccatggc taagaatctg | 3000 |
| aatgaaaaag actatgagtt gctgtgcctt gatggtacca ggaaacctgt ggaggagtat | 3060 |
| gcgaactgcc acctggccag agccccgaat cacgctgtgg tcacacggaa agataaggaa | 3120 |
| gcttgcgtcc acaagatatt acgtcaacag cagcacctat ttggaagcaa cgtaactgac | 3180 |
| tgctcgggca acttttgttt gttccggtcg gaaaccaagg accttctgtt cagagatgac | 3240 |
| acagtatgtt tggccaaact tcatgacaga aacacatatg aaaaatactt aggagaagaa | 3300 |
| tatgtcaagg ctgttggtaa cctgagaaaa tgctccacct catcactcct ggaagcctgc | 3360 |
| actttccgta gaccttaa | 3378 |

<210> SEQ ID NO 14
<211> LENGTH: 3387
<212> TYPE: DNA
<213> ORGANISM: Artificial Sequence
<220> FEATURE:
<223> OTHER INFORMATION: gene sequence encoding FVII-GS1-Tf protein
<220> FEATURE:
<223> OTHER INFORMATION: Synthesized

<400> SEQUENCE: 14

| | |
|---|---|
| atggtctccc aggccctcag gctcctctgc cttctgcttg gcttcagggg ctgcctggct | 60 |
| gcagtcttcg taacccagga ggaagcccac ggcgtcctgc accggcgccg cgcgccaac | 120 |
| gcgttcctgg aggagctgcg gccgggctcc ctggagaggg agtgcaagga ggagcagtgc | 180 |
| tccttcgagg aggcccggga gatcttcaag gacgcggaga ggacgaagct gttctggatt | 240 |
| tcttacagtg atgggaccca gtgtgcctca gtccatgcc agaatggggg ctcctgcaag | 300 |
| gaccagctcc agtcctatat ctgcttctgc ctccctgcct cgagggccg gaactgtgag | 360 |
| acgcacaagg atgaccagct gatctgtgtg aacgagaacg gcggctgtga gcagtactgc | 420 |
| agtgaccaca cgggcaccaa cgctcctgt cggtgccacg aggggtactc tctgctggca | 480 |
| gacggggtgt cctgcacacc cacagttgaa tatccatgtg gaaaaatacc tattctagaa | 540 |
| aaaagaaatg ccagcaaacc caaggccga attgtgggg gcaaggtgtg ccccaaaggg | 600 |
| gagtgtccat ggcaggtcct gttgttggtg aatggagctc agttgtgtgg ggggaccctg | 660 |
| atcaacacca tctgggtggt ctccgcggcc cactgtttcg acaaaatcaa gaactggagg | 720 |
| aacctgatcg cggtgctggg cgagcacgac ctcagcgagc acgacgggga tgagcagagc | 780 |
| cggcgggtgg cgcaggtcat catccccagc acgtacgtcc cggcaccac caaccacgac | 840 |
| atcgcgctgc tccgcctgca ccagcccgtg gtcctcactg accatgtggt gcccctctgc | 900 |
| ctgcccgaac ggacgttctc tgagaggacg ctggccttcg tgcgcttctc attggtcagc | 960 |
| ggctgggc agctgctgga ccgtggcgcc acgccctgg agctcatggt cctcaacgtg | 1020 |
| ccccggctga tgacccagga ctgcctgcag cagtcacgga aggtgggaga ctccccaaat | 1080 |
| atcacggagt acatgttctg tgccggctac tcggatggca gcaaggactc ctgcaagggg | 1140 |

```
gacagtggag gcccacatgc cacccactac cggggcacgt ggtacctgac gggcatcgtc    1200
agctggggcc agggctgcgc aaccgtgggc cactttgggg tgtacaccag ggtctcccag    1260
tacatcgagt ggctgcaaaa gctcatgcgc tcagagccac gcccaggagt cctcctgcga    1320
gccccatttc ccgtggagg cggatccgtc cctgataaaa ctgtgagatg tgtgtgcagtg    1380 tcggagcatg aggccactaa gtgccagagt ttccgcgacc atatgaaaag cgtcattcca    1440
tccgatggtc ccagtgttgc ttgtgtgaag aaagcctcct accttgattg catcagggcc    1500
attgcggcaa acgaagcgga tgctgtgaca ctggatcag gtttggtgta tgatgcttac    1560
ctggctccca ataacctgaa gcctgtggtg gcagagttct atgggtcaaa agaggatcca    1620
cagactttct attatgctgt tgctgtggtg aagaaggata gtggcttcca gatgaaccag    1680
cttcgaggca agaagtcctg ccacacgggt ctaggcaggt ccgctgggtg gaacatcccc    1740
ataggcttac tttactgtga cttacctgag ccacgtaaac ctcttgagaa agcagtggcc    1800
aatttcttct cggcagctg tgcccccttgt gcggatggga cggacttccc ccagctgtgt    1860
caactgtgtc cagggtgtgg ctgctccacc cttaaccaat acttcggcta ctcaggagcc    1920
ttcaagtgtc tgaaggatgg tgctgggat gtggcctttg tcaagcactc gactatattt    1980
gagaacttgg caaacaaggc tgacagggac cagtatgagc tgctttgcct ggacaacacc    2040
cggaagccgg tagtgaata caaggactgc cacttggccc aggtcccttc tcataccgtc    2100
gtggcccgaa gtatgggcgg caaggaggac ttgatctggg agcttctcaa ccaggcccag    2160
gaacattttg gcaaagacaa atcaaaagaa ttccaactat tcagctctcc tcatgggaag    2220
gacctgctgt ttaaggactc tgcccacggg tttttaaaag tccccccccag gatggatgcc    2280 aagatgtacc tgggctatga gtatgtcact gccatccgga atctacggga aggcacatgc    2340
ccagaagccc aacagatga atgcaagcct gtgaagtggt gtgcgctgag ccaccacgag    2400
aggctcaagt gtgatgagtg gagtgttaac agtgtaggga aatagagtg tgtatcagca    2460 gagaccaccg aagactgcat cgccaagatc atgaatggag aagctgatgc catgagcttg    2520
gatggagggt ttgtctacat agcgggcaag tgtggtctgg tgcctgtctt ggcagaaaac    2580
tacaataaga gcgataattg tgaggataca ccagaggcag ggtattttgc tgtagcagtg    2640
gtgaagaaat cagcttctga cctcacctgg gacaatctga aaggcaagaa gtcctgccat    2700
acggcagttg gcagaaccgc tggctggaac atccccatgg gcctgctcta caataagatc    2760
aaccactgca gatttgatga atttttcagt gaaggttgtg cccctgggtc taagaaagac    2820
tccagtctct gtaagctgtg tatgggctca ggcctaaacc tgtgtgaacc caacaacaaa    2880
gagggatact acggctacac aggcgctttc aggtgtctgg ttgagaaggg agatgtggcc    2940
tttgtgaaac accagactgt cccacagaac actggggaa aaaaccctga tccatgggct    3000
aagaatctga atgaaaaaga ctatgagttg ctgtgccttg atggtaccag gaaacctgtg    3060
gaggagtatg cgaactgcca cctggccaga gccccgaatc acgctgtggt cacacgaaaa    3120
gataaggaag cttgcgtcca aagatatta cgtcaacagc agcacctatt tggaagcaac    3180
gtaactgact gctcgggcaa cttttgtttg ttccggtcgg aaaccaagga ccttctgttc    3240
agagatgaca cagtatgttt ggccaaactt catgacagaa acacatatga aaatactta    3300 ggagaagaat atgtcaaggc tgttggtaac ctgagaaaat gctccacctc atcactcctg    3360
gaagcctgca ctttccgtag accttaa                                       3387
```

<210> SEQ ID NO 15

```
<211> LENGTH: 3426
<212> TYPE: DNA
<213> ORGANISM: Artificial Sequence
<220> FEATURE:
<223> OTHER INFORMATION: gene sequence encoding FVII-GS3-Tf protein
<220> FEATURE:
<223> OTHER INFORMATION: Synthesized

<400> SEQUENCE: 15
```

| | | | | |
|---|---|---|---|---|
| atggtctccc | aggccctcag | gctcctctgc | cttctgcttg | ggcttcaggg ctgcctggct | 60 |
| gcagtcttcg | taacccagga | ggaagcccac | ggcgtcctgc | accggcgccg gcgcgccaac | 120 |
| gcgttcctgg | aggagctgcg | gccgggctcc | ctggagaggg | agtgcaagga ggagcagtgc | 180 |
| tccttcgagg | aggcccggga | gatcttcaag | gacgcggaga | ggacgaagct gttctggatt | 240 |
| tcttacagtg | atgggaccca | gtgtgcctca | gtccatgcc | agaatggggg ctcctgcaag | 300 |
| gaccagctcc | agtcctatat | ctgcttctgc | ctccctgcct | tcgagggccg gaactgtgag | 360 |
| acgcacaagg | atgaccagct | gatctgtgtg | aacgagaacg | gcggctgtga gcagtactgc | 420 |
| agtgaccaca | cgggcaccaa | gcgctcctgt | cggtgccacg | aggggtactc tctgctggca | 480 |
| gacggggtgt | cctgcacacc | cacagttgaa | tatccatgtg | gaaaaatacc tattctagaa | 540 |
| aaaagaaatg | ccagcaaacc | ccaaggccga | attgtggggg | gcaaggtgtg ccccaaaggg | 600 |
| gagtgtccat | ggcaggtcct | gttgttggtg | aatggagctc | agttgtgtgg ggggaccctg | 660 |
| atcaacacca | tctgggtggt | ctccgcggcc | cactgtttcg | acaaaatcaa gaactggagg | 720 |
| aacctgatcg | cggtgctggg | cgagcacgac | ctcagcgagc | acgacgggga tgagcagagc | 780 |
| cggcgggtgg | cgcaggtcat | catccccagc | acgtacgtcc | cgggcaccac caaccacgac | 840 |
| atcgcgctgc | tccgcctgca | ccagcccgtg | gtcctcactg | accatgtggt gcccctctgc | 900 |
| ctgcccgaac | ggacgttctc | tgagaggacg | ctggccttcg | tgcgcttctc attggtcagc | 960 |
| ggctggggcc | agctgctgga | ccgtggcgcc | acggccctgg | agctcatggt cctcaacgtg | 1020 |
| ccccggctga | tgacccagga | ctgcctgcag | cagtcacgga | aggtgggaga ctccccaaat | 1080 |
| atcacggagt | acatgttctg | tgccggctac | tcggatggca | gcaaggactc ctgcaagggg | 1140 |
| gacagtggag | gccacatgc | cacccactac | cggggcacgt | ggtacctgac gggcatcgtc | 1200 |
| agctggggcc | agggctgcgc | aaccgtgggc | cactttgggg | tgtacaccag ggtctcccag | 1260 |
| tacatcgagt | ggctgcaaaa | gctcatgcgc | tcagagccac | gcccaggagt cctcctgcga | 1320 |
| gccccatttc | ccaccggtgg | aggcggttca | ggcggaggtg | gctctggcgg tggcggatcc | 1380 |
| accggtgtcc | ctgataaaac | tgtgagatgg | tgtgcagtgt | cggagcatga ggccactaag | 1440 |
| tgccagagtt | tccgcgacca | tatgaaaagc | gtcattccat | ccgatggtcc cagtgttgct | 1500 |
| tgtgtgaaga | aagcctccta | ccttgattgc | atcagggcca | ttgcggcaaa cgaagcggat | 1560 |
| gctgtgacac | tggatgcagg | tttggtgtat | gatgcttacc | tggctcccaa taacctgaag | 1620 |
| cctgtggtgg | cagagttcta | tgggtcaaaa | gaggatccac | agactttcta ttatgctgtt | 1680 |
| gctgtggtga | agaaggatag | tggcttccag | atgaaccagc | ttcgaggcaa gaagtcctgc | 1740 |
| cacacgggtc | taggcaggtc | cgctgggtgg | aacatcccca | taggcttact ttactgtgac | 1800 |
| ttacctgagc | cacgtaaacc | tcttgagaaa | gcagtggcca | atttcttctc gggcagctgt | 1860 |
| gccccttgtg | cggatgggac | ggacttcccc | cagctgtgtc | aactgtgtcc agggtgtggc | 1920 |
| tgctccaccc | ttaaccaata | cttcggctac | tcaggagcct | tcaagtgtct gaaggatggt | 1980 |
| gctggggatg | tggcctttgt | caagcactcg | actatatttg | agaacttggc aaacaaggct | 2040 |
| gacagggacc | agtatgagct | gctttgcctg | gacaacaccc | ggaagccggt agatgaatac | 2100 |

```
aaggactgcc acttggccca ggtcccttct cataccgtcg tggcccgaag tatgggcggc    2160
aaggaggact tgatctggga gcttctcaac caggcccagg aacattttgg caaagacaaa    2220
tcaaaagaat ccaactatt cagctctcct catgggaagg acctgctgtt taaggactct     2280
gcccacgggt ttttaaaagt ccccccccagg atggatgcca agatgtacct gggctatgag   2340
tatgtcactg ccatccggaa tctacgggaa ggcacatgcc cagaagcccc aacagatgaa    2400
tgcaagcctg tgaagtggtg tgcgctgagc caccacgaga ggctcaagtg tgatgagtgg    2460
agtgttaaca gtgtagggaa aatagagtgt gtatcagcag agaccaccga agactgcatc    2520
gccaagatca tgaatggaga agctgatgcc atgagcttgg atggagggtt tgtctacata    2580
gcgggcaagt gtggtctggt gcctgtcttg gcagaaaact acaataagag cgataattgt    2640
gaggatacac cagaggcagg gtattttgct gtagcagtgg tgaagaaatc agcttctgac    2700
ctcacctggg acaatctgaa aggcaagaag tcctgccata cggcagttgg cagaaccgct    2760
ggctggaaca tccccatggg cctgctctac aataagatca accactgcag atttgatgaa    2820
tttttcagtg aaggttgtgc ccctgggtct aagaaagact ccagtctctg taagctgtgt    2880
atgggctcag gcctaaacct gtgtgaaccc aacaacaaag agggatacta cggctacaca    2940
ggcgctttca ggtgtctggt tgagaaggga gatgtggcct ttgtgaaaca ccagactgtc    3000
ccacagaaca ctgggggaaa aaaccctgat ccatgggcta agaatctgaa tgaaaaagac    3060
tatgagttgc tgtgccttga tggtaccagg aaacctgtgg aggagtatgc gaactgccac    3120
ctggccagag ccccgaatca cgctgtggtc acacggaaag ataaggaagc ttgcgtccac    3180
aagatattac gtcaacagca gcacctattt ggaagcaacg taactgactg ctcgggcaac    3240
ttttgtttgt tccggtcgga aaccaaggac cttctgttca gagatgacac agtatgtttg    3300
gccaaacttc atgacagaaa cacatatgaa aaatacttag gagaagaata tgtcaaggct    3360
gttggtaacc tgagaaaatg ctccacctca tcactcctgg aagcctgcac tttccgtaga    3420
ccttaa                                                                3426

<210> SEQ ID NO 16
<211> LENGTH: 3456
<212> TYPE: DNA
<213> ORGANISM: Artificial Sequence
<220> FEATURE:
<223> OTHER INFORMATION: gene sequence encoding FVII-GS5-Tf protein
<220> FEATURE:
<223> OTHER INFORMATION: Synthesized

<400> SEQUENCE: 16
atggtctccc aggccctcag gctcctctgc cttctgcttg gcttcagggg ctgcctggct    60
gcagtcttcg taaccagga ggaagcccac ggcgtcctgc accggcgccg gcgcgccaac     120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca gtccatgcca gaatgggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480 gacgggtgt cctgcacacc cacagttgaa tatccatgtg gaaaaatacc tattctagaa      540 aaagaaatg ccagcaaacc ccaaggccga attgtggggg gcaaggtgtg ccccaaaggg      600
```

```
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctcccccaaat   1080 atcacggagt acatgttctg tgccggctac tcggatggca gcaaggactc ctgcaagggg   1140
gacagtggag ccccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccaccggtgg aggcggttca ggcggaggtg gctctggcgg tggcggatct   1380
ggcggaggtg gctctggcgg tggcggatcc accggtgtcc ctgataaaac tgtgagatgg   1440
tgtgcagtgt cggagcatga ggccactaag tgccagagtt ccgcgaccat atgaaaagc   1500 gtcattccat ccgatggtcc cagtgttgct tgtgtgaaga agcctccta ccttgattgc    1560 atcagggcca ttgcggcaaa cgaagcggat gctgtgacac tggatgcagg tttggtgtat   1620
gatgcttacc tggctcccaa taacctgaag cctgtggtgg cagagttcta tgggtcaaaa   1680
gaggatccac agactttcta ttatgctgtt gctgtggtga agaaggatag tggcttccag   1740
atgaaccagc ttcgaggcaa gaagtcctgc cacacgggtc taggcaggtc cgctgggtgg   1800
aacatcccca taggcttact ttactgtgac ttacctgagc cacgtaaacc tcttgagaaa   1860
gcagtggcca atttcttctc gggcagctgt gccccttgtg cggatgggac ggacttcccc   1920
cagctgtgtc aactgtgtcc agggtgtggc tgctccaccc ttaaccaata cttcggctac   1980
tcaggagcct tcaagtgtct gaaggatggt gctggggatg tggcctttgt caagcactcg   2040
actatatttg agaacttggc aaacaaggct gacagggacc agtatgagct gctttgcctg   2100
gacaacaccc ggaagccggt agatgaatac aaggactgcc acttggccca ggtcccttct   2160
cataccgtcg tggcccgaag tatgggcggc aaggaggact tgatctggga gcttctcaac   2220
caggcccagg aacattttgg caaagacaaa tcaaagaat tccaactatt cagctctcct   2280
catgggaagg acctgctgtt taaggactct gcccacgggt ttttaaaagt ccccccccagg   2340 atggatgcca agatgtacct gggctatgag tatgtcactg ccatccggaa tctacgggaa   2400
ggcacatgcc cagaagcccc aacagatgaa tgcaagcctg tgaagtggtg tgcgctgagc   2460
caccacgaga ggctcaagtg tgatgagtgg agtgttaaca gtgtagggaa aatagagtgt   2520
gtatcagcag agaccaccga agactgcatc gccaagatca tgaatggaga agctgatgcc   2580
atgagcttgg atggagggtt tgtctacata gcgggcaagt gtggtctggt gcctgtcttg   2640
gcagaaaact acaataagag cgataattgt gaggatacac cagaggcagg gtattttgct   2700
gtagcagtgg tgaagaaatc agcttctgac ctcacctggg acaatctgaa aggcaagaag   2760
tcctgccata cggcagttgg cagaaccgct ggctggaaca tccccatggg cctgctctac   2820
aataagatca accactgcag atttgatgaa ttttcagtg aaggttgtgc ccctgggtct   2880
aagaaagact ccagtctctg taagctgtgt atgggctcag gcctaaacct gtgtgaaccc   2940
aacaacaaag agggatacta cggctacaca ggcgctttca ggtgtctggt tgagaaggga   3000
```

```
gatgtggcct tgtgaaaaca ccagactgtc ccacagaaca ctgggggaaa aaaccctgat    3060
ccatgggcta agaatctgaa tgaaaaagac tatgagttgc tgtgccttga tggtaccagg    3120
aaacctgtgg aggagtatgc gaactgccac ctggccagag ccccgaatca cgctgtggtc    3180
acacggaaag ataaggaagc ttgcgtccac aagatattac gtcaacagca gcacctattt    3240
ggaagcaacg taactgactg ctcgggcaac ttttgtttgt tccggtcgga aaccaaggac    3300
cttctgttca gagatgacac agtatgtttg gccaaacttc atgacagaaa acatatgaa     3360 aaatacttag gagaagaata tgtcaaggct gttggtaacc tgagaaaatg ctccacctca    3420
tcactcctgg aagcctgcac tttccgtaga ccttaa                              3456
```

<210> SEQ ID NO 17
<211> LENGTH: 3486
<212> TYPE: DNA
<213> ORGANISM: Artificial Sequence
<220> FEATURE:
<223> OTHER INFORMATION: gene sequence encoding FVII-GS7-Tf protein
<220> FEATURE:
<223> OTHER INFORMATION: Synthesized

<400> SEQUENCE: 17

```
atggtctccc aggccctcag gctcctctgc cttctgcttg gcttcagggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atggggacca gtgtgcctca gtccatgcc agaatggggg ctcctgcaag     300
gaccagctcc agtcctatat ctgcttctgc ctccctgcct tcgagggccg gaactgtgag     360
acgcacaagg atgaccagct gatctgtgtg aacgagaacg gcggctgtga gcagtactgc     420
agtgaccaca cgggcaccaa gcgctcctgt cggtgccacg aggggtactc tctgctggca     480
gacggggtgt cctgcacacc cacagttgaa tatccatgtg gaaaaatacc tattctagaa     540
aaaagaaatg ccagcaaaac ccaaggccga attgtggggg caaggtgtg ccccaaaggg      600 gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gccaggagtc ctcctgcga    1320 gccccatttc ccaccggtgg aggcggttca ggcggaggtg gctctggcgg tggcggatct   1380
ggcggaggtg gctctggcgg tggcggatct ggcggaggtg gctctggcgg tggcggatcc   1440
accggtgtcc ctgataaaac tgtgagatgg tgtgcagtgt cggagcatga ggccactaag   1500
```

```
tgccagagtt ccgcgacca tatgaaaagc gtcattccat ccgatggtcc cagtgttgct   1560
tgtgtgaaga aagcctccta ccttgattgc atcagggcca ttgcggcaaa cgaagcggat   1620
gctgtgacac tggatgcagg tttggtgtat gatgcttacc tggctcccaa taacctgaag   1680
cctgtggtgg cagagttcta tgggtcaaaa gaggatccac agactttcta ttatgctgtt   1740
gctgtggtga agaaggatag tggcttccag atgaaccagc ttcgaggcaa gaagtcctgc   1800
cacacgggtc taggcaggtc cgctgggtgg aacatcccca taggcttact ttactgtgac   1860
ttacctgagc cacgtaaacc tcttgagaaa gcagtggcca atttcttctc gggcagctgt   1920
gccccttgtg cggatgggac ggacttcccc cagctgtgtc aactgtgtcc agggtgtggc   1980
tgctccaccc ttaaccaata cttcggctac tcaggagcct tcaagtgtct gaaggatggt   2040
gctggggatg tggcctttgt caagcactcg actatatttg agaacttggc aaacaaggct   2100
gacagggacc agtatgagct gctttgcctg acaacaccc ggaagccggt agatgaatac   2160
aaggactgcc acttggccca ggtcccttct cataccgtcg tggcccgaag tatgggcggc   2220
aaggaggact tgatctggga gcttctcaac caggcccagg aacattttgg caaagacaaa   2280
tcaaaagaat ccaactatt cagctctcct catgggaagg acctgctgtt taaggactct   2340
gcccacgggt ttttaaaagt cccccccagg atggatgcca agatgtacct gggctatgag   2400
tatgtcactg ccatccggaa tctacgggaa ggcacatgcc agaagcccc aacagatgaa   2460 tgcaagcctg tgaagtggtg tgcgctgagc caccacgaga ggctcaagtg tgatgagtgg   2520
agtgttaaca gtgtagggaa aatagagtgt gtatcagcag agaccaccga agactgcatc   2580
gccaagatca tgaatggaga agctgatgcc atgagcttgg atggagggtt tgtctacata   2640
gcgggcaagt gtggtctggt gcctgtcttg gcagaaaact acaataagag cgataattgt   2700
gaggatacac cagaggcagg gtattttgct gtagcagtgg tgaagaaatc agcttctgac   2760
ctcacctggg acaatctgaa aggcaagaag tcctgccata cggcagttgg cagaaccgct   2820
ggctggaaca tccccatggg cctgctctac aataagatca accactgcag atttgatgaa   2880
tttttcagtg aaggttgtgc ccctgggtct aagaaagact ccagtctctg taagctgtgt   2940
atgggctcag gcctaaacct gtgtgaaccc aacaacaaag agggatacta cggctacaca   3000
ggcgctttca ggtgtctggt tgagaaggga gatgtggcct ttgtgaaaca ccagactgtc   3060
ccacagaaca ctgggggaaa aaaccctgat ccatgggcta agaatctgaa tgaaaaagac   3120
tatgagttgc tgtgccttga tggtaccagg aaacctgtgg aggagtatgc gaactgccac   3180
ctggccagag ccccgaatca cgctgtggtc acacggaaag ataaggaagc ttgcgtccac   3240
aagatattac gtcaacagca gcacctattt ggaagcaacg taactgactg ctcgggcaac   3300
ttttgtttgt tccggtcgga aaccaaggac cttctgttca gagatgacac agtatgtttg   3360
gccaaacttc atgacagaaa cacatatgaa aaatacttag gagaagaata tgtcaaggct   3420
gttggtaacc tgagaaaatg ctccacctca tcactcctgg aagcctgcac tttccgtaga   3480
ccttaa                                                             3486
```

<210> SEQ ID NO 18
<211> LENGTH: 3516
<212> TYPE: DNA
<213> ORGANISM: Artificial Sequence
<220> FEATURE:
<223> OTHER INFORMATION: gene sequence encoding FVII-GS9-Tf protein
<220> FEATURE:
<223> OTHER INFORMATION: Synthesized

<400> SEQUENCE: 18

-continued

```
atggtctccc aggccctcag gctcctctgc cttctgcttg ggcttcaggg ctgcctggct    60
gcagtcttcg taacccagga ggaagcccac ggcgtcctgc accggcgccg gcgcgccaac   120
gcgttcctgg aggagctgcg gccgggctcc ctggagaggg agtgcaagga ggagcagtgc   180
tccttcgagg aggcccggga gatcttcaag gacgcggaga ggacgaagct gttctggatt   240
tcttacagtg atggggacca gtgtgcctca agtccatgcc agaatggggg ctcctgcaag   300
gaccagctcc agtcctatat ctgcttctgc ctccctgcct tcgagggccg gaactgtgag   360
acgcacaagg atgaccagct gatctgtgtg aacgagaacg gcggctgtga gcagtactgc   420
agtgaccaca cgggcaccaa cgctcctgt cggtgccacg aggggtactc tctgctggca    480
gacggggtgt cctgcacacc cacagttgaa tatccatgtg aaaaatacc tattctagaa    540
aaagaaatg ccagcaaacc ccaaggccga attgtggggg caaggtgtg ccccaaaggg     600
gagtgtccat ggcaggtcct gttgttggtg aatggagctc agttgtgtgg ggggaccctg   660
atcaacacca tctgggtggt ctccgcggcc cactgtttcg acaaaatcaa gaactggagg   720
aacctgatcg cggtgctggg cgagcacgac ctcagcgagc acgacgggga tgagcagagc   780
cggcgggtgg cgcaggtcat catccccagc acgtacgtcc cgggcaccac caaccacgac   840
atcgcgctgc tccgcctgca ccagcccgtg gtcctcactg accatgtggt gcccctctgc   900
ctgcccgaac ggacgttctc tgagaggacg ctggccttcg tgcgcttctc attggtcagc   960
ggctggggcc agctgctgga ccgtggcgcc acggccctgg agctcatggt cctcaacgtg  1020
ccccggctga tgacccagga ctgcctgcag cagtcacgga aggtgggaga ctccccaaat  1080
atcacggagt acatgttctg tgccggctac tcggatggca gcaaggactc ctgcaagggg  1140
gacagtggag gcccacatgc cacccactac cggggcacgt ggtacctgac gggcatcgtc  1200
agctggggcc agggctgcgc aaccgtgggc cactttgggg tgtacaccag ggtctcccag  1260
tacatcgagt ggctgcaaaa gctcatgcgc tcagagccac gcccaggagt cctcctgcga  1320
gccccatttc ccaccggtgg aggcggttca ggcggaggtg gctctggcgg tggcggatct  1380
ggcggaggtg gctctggcgg tggcggatct ggcggaggtg gctctggcgg tggcggatct  1440
ggcggaggtg gctctggcgg tggcggatcc accggtgtcc ctgataaaac tgtgagatgg  1500
tgtgcagtgt cggagcatga ggccactaag tgccagagtt ccgcgaccat tatgaaaagc  1560
gtcattccat ccgatggtcc cagtgttgct tgtgtgaaga agcctcctac ccttgattgc  1620
atcagggcca ttgcggcaaa cgaagcggat gctgtgacac tggatgcagg tttggtgtat  1680
gatgcttacc tggctcccaa taacctgaag cctgtggtgg cagagttcta tgggtcaaaa  1740
gaggatccac agacttacta ttatgctgtt gctgtggtga agaaggatag tggcttccag  1800
atgaaccagc ttcgaggcaa gaagtcctgc cacacgggtc taggcaggtc cgctgggtgg  1860
aacatcccca taggcttact ttactgtgac ttacctgagc cacgtaaacc tcttgagaaa  1920
gcagtggcca atttcttctc gggcagctgt gccccttgtg cggatgggac ggacttcccc  1980
cagctgtgtc aactgtgtcc agggtgtggc tgctccaccc ttaaccaata cttcggctac  2040
tcaggagcct tcaagtgtct gaaggatggt gctgggatg tggcctttgt caagcactcg   2100
actatatttg agaacttggc aaacaaggct gacagggacc agtatgagct gctttgcctg  2160
gacaacaccc ggaagccggt agatgaatac aaggactgcc acttggccca ggtccctctt  2220
catacctgtcg tggcccgaag tatggcggc aaggaggact tgatctggga gcttctcaac   2280
caggcccagg aacattttgg caaagacaaa tcaaagaat tccaactatt cagctctcct  2340
```

```
catgggaagg acctgctgtt taaggactct gcccacgggt ttttaaaagt cccccccagg    2400
atggatgcca agatgtacct gggctatgag tatgtcactg ccatccggaa tctacgggaa    2460
ggcacatgcc cagaagcccc aacagatgaa tgcaagcctg tgaagtggtg tgcgctgagc    2520
caccacgaga ggctcaagtg tgatgagtgg agtgttaaca gtgtagggaa aatagagtgt    2580
gtatcagcag agaccaccga agactgcatc gccaagatca tgaatggaga agctgatgcc    2640
atgagcttgg atggagggtt tgtctacata gcgggcaagt gtggtctggt gcctgtcttg    2700
gcagaaaact acaataagag cgataattgt gaggatacac agaggcagg gtattttgct    2760 gtagcagtgg tgaagaaatc agcttctgac ctcacctggg acaatctgaa aggcaagaag    2820
tcctgccata cggcagttgg cagaaccgct ggctggaaca tccccatggg cctgctctac    2880
aataagatca accactgcag atttgatgaa ttttttcagtg aaggttgtgc cctgggtct    2940 aagaaagact ccagtctctg taagctgtgt atgggctcag gcctaaacct gtgtgaaccc    3000
aacaacaaag agggatacta cggctacaca ggcgctttca ggtgtctggt tgagaaggga    3060
gatgtggcct ttgtgaaaca ccagactgtc ccacagaaca ctgggggaaa aaaccctgat    3120
ccatgggcta gaatctgaa tgaaaaagac tatgagttgc tgtgccttga tggtaccagg    3180
aaacctgtgg aggagtatgc gaactgccac ctggccagag ccccgaatca cgctgtggtc    3240
acacggaaag ataaggaagc ttgcgtccac aagatattac gtcaacagca gcacctattt    3300
ggaagcaacg taactgactg ctcgggcaac ttttgtttgt tccggtcgga aaccaaggac    3360
cttctgttca gagatgacac agtatgtttg gccaaacttc atgacagaaa cacatatgaa    3420
aaatacttag gagaagaata tgtcaaggct gttggtaacc tgagaaaatg ctccacctca    3480
tcactcctgg aagcctgcac tttccgtaga ccttaa                             3516
```

<210> SEQ ID NO 19
<211> LENGTH: 3546
<212> TYPE: DNA
<213> ORGANISM: Artificial Sequence
<220> FEATURE:
<223> OTHER INFORMATION: gene sequence encoding FVII-GS11-Tf protein
<220> FEATURE:
<223> OTHER INFORMATION: Synthesized

<400> SEQUENCE: 19

```
atggtctccc aggccctcag gctcctctgc cttctgcttg ggcttcaggg ctgcctggct     60
gcagtcttcg taacccagga ggaagcccac ggcgtcctgc accggcgccg gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca gtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc caaggccga attgtggggg gcaaggtgtg ccccaaaggg    600
gagtgtccat ggcaggtcct gttgttggtg aatggagctc agttgtgtgg gggaccctg    660 atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
```

```
atcgcgctgc tccgcctgca ccagcccgtg gtcctcactg accatgtggt gccccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag gtctcccag    1260
tacatcgagt ggctgcaaaa gctcatgcgc tcagagccac gcccaggagt cctcctgcga   1320
gccccatttc ccaccggtgg aggcggttca ggcggaggtg gctctggcgg tggcggatct   1380
ggcggaggtg gctctggcgg tggcggatct ggcggaggtg gctctggcgg tggcggatct   1440
ggcggaggtg gctctggcgg tggcggatct ggcggaggtg gctctggcgg tggcggatcc   1500
accggtgtcc ctgataaaac tgtgagatgg tgtgcagtgt cggagcatga ggccactaag   1560
tgccagagtt ccgcgacca tatgaaaagc gtcattccat ccgatggtcc cagtgttgct   1620
tgtgtgaaga aagcctccta ccttgattgc atcagggcca ttgcggcaaa cgaagcggat   1680
gctgtgacac tggatgcagg tttggtgtat gatgcttacc tggctcccaa taacctgaag   1740
cctgtggtgg cagagttcta tgggtcaaaa gaggatccac agactttcta ttatgctgtt   1800
gctgtggtga agaaggatag tggcttccag atgaaccagc ttcgaggcaa gaagtcctgc   1860
cacacgggtc taggcaggtc cgctgggtgg aacatcccca taggcttact ttactgtgac   1920
ttacctgagc cacgtaaacc tcttgagaaa gcagtggcca atttcttctc gggcagctgt   1980
gccccttgtg cggatgggac ggacttcccc cagctgtgtc aactgtgtcc agggtgtggc   2040
tgctccaccc ttaaccaata cttcggctac tcaggagcct tcaagtgtct gaaggatggt   2100
gctgggggatg tggcctttgt caagcactcg actatatttg agaacttggc aaacaaggct   2160
gacagggacc agtatgagct gctttgcctg gacaacaccc ggaagccggt agatgaatac   2220
aaggactgcc acttggccca ggtccccttct cataccgtcg tggcccgaag tatgggcggc   2280
aaggaggact tgatctggga gcttctcaac caggcccagg aacattttgg caaagacaaa   2340
tcaaaagaat ccaactatt cagctctcct catgggaagg acctgctgtt taaggactct   2400
gcccacgggt tttaaaaagt ccccccccagg atggatgcca gatgtacct gggctatgag   2460
tatgtcactg ccatccggaa tctacgggaa ggcacatgcc agaagcccc aacagatgaa   2520
tgcaagcctg tgaagtggtg tgcgctgagc caccacgaga ggctcaagtg tgatgagtgg   2580
agtgttaaca gtgtagggaa aatagagtgt gtatcagcag agaccaccga agactgcatc   2640
gccaagatca tgaatggaga agctgatgcc atgagcttgg atggagggtt tgtctacata   2700
gcgggcaagt gtggtctggt gcctgtcttg gcagaaaact acaataagag cgataattgt   2760
gaggatacac cagaggcagg gtatttttgct gtagcagtgg tgaagaaatc agcttctgac   2820
ctcacctggg acaatctgaa aggcaagaag tcctgccata cggcagttgg cagaaccgct   2880
ggctggaaca tccccatggg cctgctctac aataagatca accactgcag atttgatgaa   2940
ttttccagtg aaggttgtgc ccctgggtct aagaaagact ccagtctctg taagctgtgt   3000
atgggctcag gcctaaacct gtgtgaaccc aacaacaaag agggatacta cggctacaca   3060
ggcgctttca ggtgtctggt tgagaaggga gatgtggcct tgtgaaaaca ccagactgtc   3120
ccacagaaca ctgggggaaa aaaccctgat ccatgggcta agaatctgaa tgaaaaagac   3180
```

```
tatgagttgc tgtgccttga tggtaccagg aaacctgtgg aggagtatgc gaactgccac    3240
ctggccagag ccccgaatca cgctgtggtc acacggaaag ataaggaagc ttgcgtccac    3300
aagatattac gtcaacagca gcacctattt ggaagcaacg taactgactg ctcgggcaac    3360
ttttgtttgt tccggtcgga aaccaaggac cttctgttca gagatgacac agtatgtttg    3420
gccaaacttc atgacagaaa cacatatgaa aaatacttag agaagaaata tgtcaaggct    3480
gttggtaacc tgagaaaatg ctccacctca tcactcctgg aagcctgcac tttccgtaga    3540
ccttaa                                                               3546

<210> SEQ ID NO 20
<211> LENGTH: 3576
<212> TYPE: DNA
<213> ORGANISM: Artificial Sequence
<220> FEATURE:
<223> OTHER INFORMATION: gene sequence encoding FVII-GS13-Tf protein
<220> FEATURE:
<223> OTHER INFORMATION: Synthesized

<400> SEQUENCE: 20
atggtctccc aggccctcag gctcctctgc cttctgcttg ggcttcaggg ctgcctggct      60
gcagtcttcg taacccagga ggaagcccac ggcgtcctgc accggcgccg cgcgccaac     120 gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca gtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaagaaatgc cagcaaaacc caaggccga attgtggggg caaggtgtg ccccaaaggg    600 gagtgtccat ggcaggtcct gttgttggtg aatggagctc agttgtgtgg ggggaccctg    660
atcaacacca tctgggtggt ctccgcggcc cactgttttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggcctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gccacatgc acccactac cggggcacgt ggtacctgac gggcatcgtc   1200
agctggggcc agggctgcgc aaccgtgggc cactttgggg tgtacaccag gtctcccag   1260 tacatcgagt ggctgcaaaa gctcatgcgc tcagagccac gcccaggagt cctcctgcga   1320
gccccatttc ccaccggtgg aggcggttca ggcggaggtg gctctggcgg tggcggatct   1380
ggcggaggtg gctctggcgg tggcggatct ggcggaggtg gctctggcgg tggcggatct   1440
ggcggaggtg gctctggcgg tggcggatct ggcggaggtg gctctggcgg tggcggatct   1500
ggcggaggtg gctctggcgg tggcggatcc accggtgtcc ctgataaaac tgtgagatgg   1560
tgtgcagtgt cggagcatga ggccactaag tgccagagtt ccgcgaccat atgaaaagc   1620
```

```
gtcattccat ccgatggtcc cagtgttgct tgtgtgaaga agcctccta ccttgattgc   1680 atcagggcca ttgcggcaaa cgaagcggat gctgtgacac tggatgcagg tttggtgtat   1740
gatgcttacc tggctcccaa taacctgaag cctgtggtgg cagagttcta tgggtcaaaa   1800
gaggatccac agactttcta ttatgctgtt gctgtggtga agaaggatag tggcttccag   1860
atgaaccagc ttcgaggcaa gaagtcctgc cacacgggtc taggcaggtc cgctgggtgg   1920
aacatcccca taggcttact ttactgtgac ttacctgagc cacgtaaacc tcttgagaaa   1980
gcagtggcca atttcttctc gggcagctgt gccccttgtg cggatgggac ggacttcccc   2040
cagctgtgtc aactgtgtcc agggtgtggc tgctccaccc ttaaccaata cttcggctac   2100
tcaggagcct tcaagtgtct gaaggatggt gctggggatg tggcctttgt caagcactcg   2160
actatatttg agaacttggc aaacaaggct gacaggacc agtatgagct gctttgcctg   2220
gacaacaccc ggaagccggt agatgaatac aaggactgcc acttggccca ggtcccttct   2280
cataccgtcg tggcccgaag tatgggcggc aaggaggact tgatctggga gcttctcaac   2340
caggcccagg aacattttgg caaagacaaa tcaaaagaat ccaactatt cagctctcct   2400 catgggaagg acctgctgtt taaggactct gcccacgggt ttttaaaagt ccccccagg   2460 atggatgcca agatgtacct gggctatgag tatgtcactg ccatccggaa tctacgggaa   2520
ggcacatgcc cagaagcccc aacagatgaa tgcaagcctg tgaagtggtg tgcgctgagc   2580
caccacgaga ggctcaagtg tgatgagtgg agtgttaaca gtgtagggaa aatagagtgt   2640
gtatcagcag agaccaccga agactgcatc gccaagatca tgaatggaga agctgatgcc   2700
atgagcttgg atggagggtt tgtctacata gcgggcaagt gtggtctggt gcctgtcttg   2760
gcagaaaact acaataagag cgataattgt gaggatacac cagaggcagg tatttttgct   2820
gtagcagtgg tgaagaaatc agcttctgac ctcacctggg acaatctgaa aggcaagaag   2880
tcctgccata cggcagttgg cagaaccgct ggctggaaca tccccatggg cctgctctac   2940
aataagatca ccactgcag atttgatgaa tttttcagtg aaggttgtgc ccctgggtct   3000
aagaaagact ccagtctctg taagctgtgt atgggctcag gcctaaacct gtgtgaaccc   3060
aacaacaaag agggatacta cggctacaca ggcgctttca ggtgtctggt tgagaaggga   3120
gatgtggcct ttgtgaaaca ccagactgtc ccacagaaca ctgggggaaa aaaccctgat   3180
ccatgggcta agaatctgaa tgaaaaagac tatgagttgc tgtgccttga tggtaccagg   3240
aaacctgtgg aggagtatgc gaactgccac ctggccagag ccccgaatca cgctgtggtc   3300
acacggaaag ataaggaagc ttgcgtccac aagatattac gtcaacagca gcacctattt   3360
ggaagcaacg taactgactg ctcgggcaac ttttgtttgt tccggtcgga aaccaaggac   3420
cttctgttca gagatgacac agtatgtttg gccaaacttc atgacagaaa cacatatgaa   3480
aaatacttag gagaagaata tgtcaaggct gttggtaacc tgagaaaatg ctccacctca   3540
tcactcctgg aagcctgcac tttccgtaga ccttaa                             3576
```

<210> SEQ ID NO 21
<211> LENGTH: 3606
<212> TYPE: DNA
<213> ORGANISM: Artificial Sequence
<220> FEATURE:
<223> OTHER INFORMATION: gene sequence encoding FVII-GS15-Tf protein
<220> FEATURE:
<223> OTHER INFORMATION: Synthesized

<400> SEQUENCE: 21

```
atggtctccc aggccctcag gctcctctgc cttctgcttg ggcttcaggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atggggacca gtgtgcctca agtccatgcc agaatggggg ctcctgcaag     300
gaccagctcc agtcctatat ctgcttctgc ctccctgcct tcgagggccg gaactgtgag     360
acgcacaagg atgaccagct gatctgtgtg aacgagaacg gcggctgtga gcagtactgc     420
agtgaccaca cgggcaccaa cgctcctgt cggtgccacg aggggtactc tctgctggca     480
gacgggtgt cctgcacacc cacagttgaa tatccatgtg aaaaatacc tattctagaa     540
aaaagaaatg ccagcaaacc ccaaggccga attgtggggg gcaaggtgtg ccccaaaggg     600
gagtgtccat ggcaggtcct gttgttggtg aatggagctc agttgtgtgg ggggaccctg     660
atcaacacca tctgggtggt ctccgcggcc cactgtttcg acaaaatcaa gaactggagg     720
aacctgatcg cggtgctggg cgagcacgac ctcagcgagc acgacgggga tgagcagagc     780
cggcgggtgg cgcaggtcat catccccagc acgtacgtcc cgggcaccac caaccacgac     840
atcgcgctgc tccgcctgca ccagcccgtg gtcctcactg accatgtggt gcccctctgc     900
ctgcccgaac ggacgttctc tgagaggacg ctggccttcg tgcgcttctc attggtcagc     960
ggctggggcc agctgctgga ccgtggcgcc acggccctgg agctcatggt cctcaacgtg    1020
ccccggctga tgacccagga ctgcctgcag cagtcacgga aggtgggaga ctccccaaat    1080
atcacggagt acatgttctg tgccggctac tcggatggca gcaaggactc ctgcaagggg    1140
gacagtggag gcccacatgc cacccactac cggggcacgt ggtacctgac gggcatcgtc    1200
agctggggcc agggctgcgc aaccgtgggc cactttgggg tgtacaccag ggtctcccag    1260
tacatcgagt ggctgcaaaa gctcatgcgc tcagagccac gcccaggagt cctcctgcga    1320
gccccatttc ccaccggtgg aggcggttca ggcggaggtg gctctggcgg tggcggatct    1380
ggcggaggtg gctctggcgg tggcggatct ggcggaggtg gctctggcgg tggcggatct    1440
ggcggaggtg gctctggcgg tggcggatct ggcggaggtg gctctggcgg tggcggatct    1500
ggcggaggtg gctctggcgg tggcggatct ggcggaggtg gctctggcgg tggcggatcc    1560
accggtgtcc ctgataaaac tgtgagatgg tgtgcagtgt cggagcatga ggccactaag    1620
tgccagagtt ccgcgacca tatgaaaagc gtcattccat ccgatggtcc cagtgttgct    1680
tgtgtgaaga aagcctccta ccttgattgc atcaggccca ttgcggcaaa cgaagcggat    1740
gctgtgacac tggatgcagg tttggtgtat gatgcttacc tggctcccaa taacctgaag    1800
cctgtggtgg cagagttcta tgggtcaaaa gaggatccac agactttcta ttatgctgtt    1860
gctgtggtga agaaggatag tggcttccag atgaaccagc ttcgaggcaa gaagtcctgc    1920
cacacgggtc taggcaggtc cgctgggtgg aacatcccca taggcttact ttactgtgac    1980
ttacctgagc cacgtaaacc tcttgagaaa gcagtggcca atttcttctc gggcagctgt    2040
gccccttgtg cggatgggac ggacttcccc cagctgtgtc aactgtgtcc agggtgtggc    2100
tgctccaccc ttaaccaata cttcggctac tcaggagcct tcaagtgtct gaaggatggt    2160
gctggggatg tggcctttgt caagcactcg actatatttg agaacttggc aaacaaggct    2220
gacagggacc agtatgagct gctttgcctg gacaacaccc ggaagccggt agatgaatac    2280
aaggactgcc acttggccca ggtccccttct cataccgtcg tggcccgaag tatgggcggc    2340
aaggaggact tgatctggga gcttctcaac caggcccagg aacattttgg caaagacaaa    2400
```

-continued

```
tcaaaagaat tccaactatt cagctctcct catgggaagg acctgctgtt taaggactct    2460
gcccacgggt ttttaaaagt ccccccccagg atggatgcca agatgtacct gggctatgag   2520
tatgtcactg ccatccggaa tctacgggaa ggcacatgcc cagaagcccc aacagatgaa    2580
tgcaagcctg tgaagtggtg tgcgctgagc caccacgaga ggctcaagtg tgatgagtgg    2640
agtgttaaca gtgtagggaa atagagtgt gtatcagcag agaccaccga agactgcatc     2700
gccaagatca tgaatggaga agctgatgcc atgagcttgg atggagggtt tgtctacata    2760
gcgggcaagt gtggtctggt gcctgtcttg gcagaaaact acaataagag cgataattgt    2820
gaggatacac cagaggcagg gtattttgct gtagcagtgg tgaagaaatc agcttctgac    2880
ctcacctggg acaatctgaa aggcaagaag tcctgccata cggcagttgg cagaaccgct    2940
ggctggaaca tccccatggg cctgctctac aataagatca accactgcag atttgatgaa    3000
tttttcagtg aaggttgtgc ccctgggtct aagaaagact ccagtctctg taagctgtgt    3060
atgggctcag gcctaaacct gtgtgaaccc aacaacaaag agggatacta cggctacaca    3120
ggcgctttca ggtgtctggt tgagaaggga gatgtggcct ttgtgaaaca ccagactgtc    3180
ccacagaaca ctgggggaaa aaaccctgat ccatgggcta agaatctgaa tgaaaaagac    3240
tatgagttgc tgtgccttga tggtaccagg aaacctgtgg aggagtatgc gaactgccac    3300
ctggccagag ccccgaatca cgctgtggtc acacggaaag ataaggaagc ttgcgtccac    3360
aagatattac gtcaacagca gcacctattt ggaagcaacg taactgactg ctcgggcaac    3420
ttttgtttgt tccggtcgga aaccaaggac cttctgttca gagatgacac agtatgtttg    3480
gccaaacttc atgacagaaa cacatatgaa aaatacttag gagaagaata tgtcaaggct    3540
gttggtaacc tgagaaaatg ctccacctca tcactcctgg aagcctgcac tttccgtaga    3600
ccttaa                                                               3606
```

<210> SEQ ID NO 22
<211> LENGTH: 3450
<212> TYPE: DNA
<213> ORGANISM: Artificial Sequence
<220> FEATURE:
<223> OTHER INFORMATION: gene sequence encoding FVII-Helix-Tf protein
<220> FEATURE:
<223> OTHER INFORMATION: Synthesized

<400> SEQUENCE: 22

```
atggtctccc aggccctcag gctcctctgc cttctgcttg gcttcagggg ctgcctggct     60
gcagtcttcg taacccagga ggaagcccac ggcgtcctgc accggcgcgc gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca gtccatgcc agaatggggg ctcctgcaag    300
gaccagctcc agtcctatat ctgcttctgc ctccctgcct cgagggccg aactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaatacc tattctagaa    540
aaagaaatg ccagcaaacc ccaaggccga attgtggggg gcaaggtgtg ccccaaaggg    600
gagtgtccat ggcaggtcct gttgttgtg aatggagctc agttgtgtgg ggggaccctg    660
atcaacacca tctgggtggt ctccgcggcc cactgtttcg acaaaatcaa gaactggagg    720
```

```
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccaccggtgc tgaagctgca gccaagaaag ctgcagccaa agaggccgca   1380
gctaaggaag ccgcagcaaa agctaccggt gtccctgata aaactgtgag atggtgtgca   1440
gtgtcggagc atgaggccac taagtgccag agtttccgcg accatatgaa aagcgtcatt   1500
ccatccgatg gtcccagtgt tgcttgtgtg aagaaagcct cctaccttga ttgcatcagg   1560
gccattgcgg caaacgaagc ggatgctgtg acactggatg caggtttggt gtatgatgct   1620
tacctggctc ccaataacct gaagcctgtg gtggcagagt tctatgggtc aaaagaggat   1680
ccacagactt tctattatgc tgttgctgtg gtgaagaagg atagtggctt ccagatgaac   1740
cagcttcgag gcaagaagtc ctgccacacg ggtctaggca ggtccgctgg gtggaacatc   1800
cccataggct tactttactg tgacttacct gagccacgta aacctcttga aaagcagtg    1860 gccaatttct tctcgggcag ctgtgcccct tgtgcggatg ggacggactt ccccagctg    1920 tgtcaactgt gtccagggtg tggctgctcc acccttaacc aatacttcgg ctactcagga   1980
gccttcaagt gtctgaagga tggtgctggg gatgtggcct tgtcaagca ctcgactata    2040 tttgagaact tggcaaacaa ggctgacagg gaccagtatg agctgctttg cctggacaac   2100
acccggaagc cggtagatga atacaaggac tgccacttgg cccaggtccc ttctcatacc   2160
gtcgtggccc gaagtatggg cggcaaggag gacttgatct gggagcttct caaccaggcc   2220
caggaacatt ttggcaaaga caaatcaaaa gaattccaac tattcagctc tcctcatggg   2280
aaggacctgc tgtttaagga ctctgcccac gggttttaa aagtcccccc caggatggat    2340
gccaagatgt acctgggcta tgagtatgtc actgccatcc ggaatctacg ggaaggcaca   2400
tgcccagaag ccccaacaga tgaatgcaag cctgtgaagt ggtgtgcgct gagccaccac   2460
gagaggctca gtgtgatga gtggagtgtt aacagtgtag gaaaataga gtgtgtatca     2520 gcagagacca ccgaagactg catcgccaag atcatgaatg agaagctga tgccatgagc    2580 ttggatggag ggtttgtcta catagcgggc aagtgtggtc tggtgcctgt cttggcagaa   2640
aactacaata gagcgataa ttgtgaggat acaccagagg cagggtattt tgctgtagca    2700
gtggtgaaga aatcagcttc tgacctcacc tgggacaatc tgaaaggcaa gaagtcctgc   2760
catacggcag ttggcagaac cgctggctgg aacatcccca tgggcctgct ctacaataag   2820
atcaaccact gcagatttga tgaatttttc agtgaaggtt gtgcccctgg gtctaagaaa   2880
gactccagtc tctgtaagct gtgtatgggc tcaggcctaa acctgtgtga acccaacaac   2940
aaagagggat actacggcta cacaggcgct tcaggtgtc tggttgagaa gggagatgtg    3000
gcctttgtga acaccagac tgtcccacag aacactgggg gaaaaaccc tgatccatgg     3060 gctaagaatc tgaatgaaaa agactatgag ttgctgtgcc ttgatggtac caggaaacct   3120
```

```
gtggaggagt atgcgaactg ccacctggcc agagccccga atcacgctgt ggtcacacgg    3180
aaagataagg aagcttgcgt ccacaagata ttacgtcaac agcagcacct atttggaagc    3240
aacgtaactg actgctcggg caacttttgt ttgttccggt cggaaaccaa ggaccttctg    3300
ttcagagatg acacagtatg tttggccaaa cttcatgaca gaaacacata tgaaaaatac    3360
ttaggagaag aatatgtcaa ggctgttggt aacctgagaa aatgctccac ctcatcactc    3420
ctggaagcct gcactttccg tagaccttaa                                    3450

<210> SEQ ID NO 23
<211> LENGTH: 3426
<212> TYPE: DNA
<213> ORGANISM: Artificial Sequence
<220> FEATURE:
<223> OTHER INFORMATION: gene sequence encoding FVII-GS1-T-Tf protein
<220> FEATURE:
<223> OTHER INFORMATION: Synthesized

<400> SEQUENCE: 23
atggtctccc aggccctcag gctcctctgc cttctgcttg gcttcagggc ctgcctggct      60
gcagtcttcg taacccagga ggaagcccac ggcgtcctgc accggcgccg cgcgccaac     120 gcgttcctgg aggagctgcg gccgggctcc ctggagaggg agtgcaagga ggagcagtgc    180
tccttcgagg aggccccggga gatcttcaag gacgcggaga ggacgaagct gttctggatt    240
tcttacagtg atgggaccag tgtgcctca agtccatgcc agaatggggg ctcctgcaag     300
gaccagctcc agtcctatat ctgcttctgc ctccctgcct cgagggccg gaactgtgag     360 acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc caagggccga attgtggggg gcaaggtgtg ccccaaaggg    600
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg    1020
ccccggctga tgacccagga ctgcctgcag cagtcacgga aggtgggaga ctccccaaat    1080
atcacggagt acatgttctg tgccggctac tcggatggca gcaaggactc ctgcaagggg    1140
gacagtggag gcccacatgc cacccactac cggggcacgt ggtacctgac gggcatcgtc    1200 agctgggcc agggctgcgc aaccgtgggc cactttgggg tgtacaccag ggtctcccag    1260
tacatcgagt ggctgcaaaa gctcatgcgc tcagagccac gcccaggagt cctcctgcga    1320
gcccccattt ccaccggtgg aggcggatcc ctggtgccgc gcggcagcgg aggcggttca    1380
accggtgtcc ctgataaaac tgtgagatgg tgtgcagtgt cggagcatga ggccactaag    1440
tgccagagtt ccgcgaccat atgaaaagc gtcattccat ccgatggtcc cagtgttgct    1500
tgtgtgaaga agcctcccta ccttgattgc atcagggcca ttgcggcaaa cgaagcggat    1560
gctgtgacac tggatgcagg tttggtgtat gatgcttacc tggctcccaa taacctgaag    1620
```

```
cctgtggtgg cagagttcta tgggtcaaaa gaggatccac agactttcta ttatgctgtt    1680
gctgtggtga agaaggatag tggcttccag atgaaccagc ttcgaggcaa gaagtcctgc    1740
cacacgggtc taggcaggtc cgctgggtgg aacatcccca taggcttact ttactgtgac    1800
ttacctgagc cacgtaaacc tcttgagaaa gcagtggcca atttcttctc gggcagctgt    1860
gccccttgtg cggatgggac ggacttcccc cagctgtgtc aactgtgtcc agggtgtggc    1920
tgctccaccc ttaaccaata cttcggctac tcaggagcct tcaagtgtct gaaggatggt    1980
gctggggatg tggcctttgt caagcactcg actatatttg agaacttggc aaacaaggct    2040
gacagggacc agtatgagct gctttgcctg gacaacaccc ggaagccggt agatgaatac    2100
aaggactgcc acttggccca ggtcccttct catacgtcg tggcccgaag tatgggcggc    2160
aaggaggact tgatctggga gcttctcaac caggcccagg aacattttgg caaagacaaa    2220
tcaaaagaat tccaactatt cagctctcct catgggaagg acctgctgtt taaggactct    2280
gcccacgggt ttttaaaagt ccccccccagg atggatgcca agatgtacct gggctatgag    2340
tatgtcactg ccatccggaa tctacgggaa ggcacatgcc cagaagcccc aacagatgaa    2400
tgcaagcctg tgaagtggtg tgcgctgagc caccacgaga ggctcaagtg tgatgagtgg    2460
agtgttaaca gtgtagggaa aatagagtgt gtatcagcag agaccaccga agactgcatc    2520
gccaagatca tgaatggaga agctgatgcc atgagcttgg atggagggtt tgtctacata    2580
gcgggcaagt gtggtctggt gcctgtcttg gcagaaaact acaataagag cgataattgt    2640
gaggatacac cagaggcagg gtattttgct gtagcagtgg tgaagaaatc agcttctgac    2700
ctcacctggg acaatctgaa aggcaagaag tcctgccata cggcagttgg cagaaccgct    2760
ggctggaaca tccccatggg cctgctctac aataagatca accactgcag atttgatgaa    2820
tttttcagtg aaggttgtgc ccctgggtct aagaaagact ccagtctctg taagctgtgt    2880
atgggctcag gcctaaacct gtgtgaaccc aacaacaaag agggatacta cggctacaca    2940
ggcgctttca ggtgtctggt tgagaaggga gatgtggcct ttgtgaaaca ccagactgtc    3000
ccacagaaca ctgggggaaa aaaccctgat ccatgggcta agaatctgaa tgaaaaagac    3060
tatgagttgc tgtgccttga tggtaccagg aaacctgtgg aggagtatgc gaactgccac    3120
ctggccagag ccccgaatca cgctgtggtc acacggaaag ataaggaagc ttgcgtccac    3180
aagatattac gtcaacagca gcacctattt ggaagcaacg taactgactg ctcgggcaac    3240
ttttgtttgt tccggtcgga aaccaaggac cttctgttca gagatgacac agtatgtttg    3300
gccaaacttc atgacagaaa cacatatgaa aaatacttag gagaagaata tgtcaaggct    3360
gttggtaacc tgagaaaatg ctccacctca tcactcctgg aagcctgcac tttccgtaga    3420
ccttaa                                                              3426

<210> SEQ ID NO 24
<211> LENGTH: 3417
<212> TYPE: DNA
<213> ORGANISM: Artificial Sequence
<220> FEATURE:
<223> OTHER INFORMATION: gene sequence encoding FVII-GS1-T-Tf(M3)
      protein
<220> FEATURE:
<223> OTHER INFORMATION: Synthesized

<400> SEQUENCE: 24
atggtctccc aggccctcag gctcctctgc cttctgcttg gcttcagggg ctgcctggct      60
gcagtcttcg taacccagga ggaagcccac ggcgtcctgc accggcgccg gcgcgccaac     120
```

```
gcgttcctgg aggagctgcg gccgggctcc ctggagaggg agtgcaagga ggagcagtgc      180
tccttcgagg aggcccggga gatcttcaag gacgcggaga ggacgaagct gttctggatt      240
tcttacagtg atggggacca gtgtgcctca agtccatgcc agaatggggg ctcctgcaag      300
gaccagctcc agtcctatat ctgcttctgc ctccctgcct tcgagggccg gaactgtgag      360
acgcacaagg atgaccagct gatctgtgtg aacgagaacg gcggctgtga gcagtactgc      420
agtgaccaca cgggcaccaa cgctcctgt cggtgccacg aggggtactc tctgctggca      480 gacgggtgt cctgcacacc cacagttgaa tatccatgtg aaaaatacc tattctagaa      540 aaagaaatg ccagcaaacc caaggccga attgtggggg gcaaggtgtg ccccaaaggg      600
gagtgtccat ggcaggtcct gttgttggtg aatggagctc agttgtgtgg ggggacccctg     660 atcaacacca tctgggtggt ctccgcggcc cactgtttcg acaaaatcaa gaactggagg      720
aacctgatcg cggtgctggg cgagcacgac ctcagcgagc acgacgggga tgagcagagc      780
cggcgggtgg cgcaggtcat catccccagc acgtacgtcc cgggcaccac caaccacgac      840
atcgcgctgc tccgcctgca ccagcccgtg gtcctcactg accatgtggt gcccctctgc      900
ctgcccgaac ggacgttctc tgagaggacg ctggccttcg tgcgcttctc attggtcagc      960
ggctggggcc agctgctgga ccgtggcgcc acggccctgg agctcatggt cctcaacgtg     1020
ccccggctga tgacccagga ctgcctgcag cagtcacgga aggtgggaga ctccccaaat     1080
atcacggagt acatgttctg tgccggctac tcggatggca gcaaggactc ctgcaagggg     1140
gacagtggag gcccacatgc cacccactac cggggcacgt ggtacctgac gggcatcgtc     1200
agctggggcc agggctgcgc aaccgtgggc cactttgggg tgtacaccag ggtctcccag     1260
tacatcgagt ggctgcaaaa gctcatgcgc tcagagccac gcccaggagt cctcctgcga     1320
gccccatttc ccggtggagg cggatccctg gtgccgcgcg gcagcggagg cggttcagtc     1380
cctgataaaa ctgtgagatg gtgtgcagtg tcggagcatg aggccactaa gtgccagagt     1440
ttccgcgacc atatgaaaag cgtcattcca tccgatggtc ccagtgttgc ttgtgtgaag     1500
aaagcctcct accttgattg catcagggcc attgcggcaa acgaagcgga tgctgtgaca     1560
ctggatgcag gtttggtgta tgatgcttac ctggctccca taacctgaa gcctgtggtg     1620 gcagagttct atgggtcaaa agaggatcca cagactttct attatgctgt tgctgtggtg     1680
aagaaggata gtggcttcca gatgaaccag cttcgaggca agaagtcctg ccacacgggt     1740
ctaggcaggt ccgctgggtg gaacatcccc ataggcttac tttactgtga cttacctgag     1800
ccacgtaaac ctcttgagaa agcagtggcc aatttcttct cgggcagctg tgccccttgt     1860
gcggatggga cggacttccc ccagctgtgt caactgtgtc cagggtgtgg ctgctccacc     1920
cttaaccaat acttcggcta ctcaggagcc ttcaagtgtc tgaaggatgg tgctggggat     1980
gtggcctttg tcaagcactc gactatattt gagaacttgg caaacaaggc tgacagggac     2040
cagtatgagc tgctttgcct ggacaacacc cggaagccgg tagatgaata caaggactgc     2100
cacttggccc aggtcccttc tcataccgtc gtggcccgaa gtatgggcgg caaggaggac     2160
ttgatctggg agcttctcaa ccaggcccag gaacattttg gcaaagacaa atcaaaagaa     2220
ttccaactat tcagctctcc tcatgggaag gacctgctgt ttaaggactc tgcccacggg     2280
ttttttaaag tccccccag gatggatgcc aagatgtacc tgggctatga gtatgtcact     2340
gccatccgga atctacggga aggcacatgc ccagaagccc caacagatga atgcaagcct     2400
gtgaagtggt gtgcgctgag ccaccacgag aggctcaagt gtgatgagtg gagtgttaac     2460
agtgtaggga aaatagagtg tgtatcagca gagaccaccg aagactgcat cgccaagatc     2520
```

```
atgaatggag aagctgatgc catgagcttg gatggagggt ttgtctacat agcgggcaag    2580
tgtggtctgg tgcctgtctt ggcagaaaac tacaataaga gcgataattg tgaggataca    2640
ccagaggcag ggtattttgc tgtagcagtg gtgaagaaat cagcttctga cctcacctgg    2700
gacaatctga aaggcaagaa gtcctgccat acggcagttg cagaaccgc tggctggaac     2760 atccccatgg gcctgctcta caataagatc aaccactgca gatttgatga attttttcagt   2820 gaaggttgtg cccctgggtc taagaaagac tccagtctct gtaagctgtg tatgggctca    2880
ggcctaaacc tgtgtgaacc caacaacaaa gagggatact acggctacac aggcgctttc    2940
aggtgtctgg ttgagaaggg agatgtggcc tttgtgaaac accagactgt cccacagaac    3000
actgggggaa aaaccctga tccatgggct aagaatctga tgaaaaaga ctatgagttg       3060 ctgtgccttg atggtaccag gaaacctgtg gaggagtatg cgaactgcca cctggccaga    3120
gccccgaatc acgctgtggt cacacggaaa gataaggaag cttgcgtcca agatatta     3180 cgtcaacagc agcacctatt tggaagcaac gtaactgact gctcgggcaa cttttgtttg   3240
ttccggtcgg aaaccaagga ccttctgttc agagatgaca cagtatgttt ggccaaactt   3300
catgacagaa acacatatga aaaatactta ggagaagaat atgtcaaggc tgttggtaac    3360
ctgagaaaat gctccacctc atcactcctg gaagcctgca ctttccgtag accttaa       3417
```

<210> SEQ ID NO 25
<211> LENGTH: 25
<212> TYPE: DNA
<213> ORGANISM: Artificial Sequence
<220> FEATURE:
<223> OTHER INFORMATION: FVII-F primer
<220> FEATURE:
<223> OTHER INFORMATION: Synthesized

<400> SEQUENCE: 25
aggggcagca ctgcagagat ttcat                                          25

<210> SEQ ID NO 26
<211> LENGTH: 25
<212> TYPE: DNA
<213> ORGANISM: Artificial Sequence
<220> FEATURE:
<223> OTHER INFORMATION: FVII-R primer
<220> FEATURE:
<223> OTHER INFORMATION: Synthesized

<400> SEQUENCE: 26
tatgggattt ggtgccagga cagtt                                          25

<210> SEQ ID NO 27
<211> LENGTH: 31
<212> TYPE: DNA
<213> ORGANISM: Artificial Sequence
<220> FEATURE:
<223> OTHER INFORMATION: FVII-S1 primer
<220> FEATURE:
<223> OTHER INFORMATION: Synthesized

<400> SEQUENCE: 27
aattgctagc atggtctccc aggccctcag g                                   31

<210> SEQ ID NO 28
<211> LENGTH: 31
<212> TYPE: DNA
<213> ORGANISM: Artificial Sequence
<220> FEATURE:

```
<223> OTHER INFORMATION: FVII-AS1 primer
<220> FEATURE:
<223> OTHER INFORMATION: Synthesized

<400> SEQUENCE: 28
aattaccggt gggaaatggg gctcgcagga g                              31

<210> SEQ ID NO 29
<211> LENGTH: 33
<212> TYPE: DNA
<213> ORGANISM: Artificial Sequence
<220> FEATURE:
<223> OTHER INFORMATION: Tf-S1 primer
<220> FEATURE:
<223> OTHER INFORMATION: Synthesized

<400> SEQUENCE: 29
atataccggt gtccctgata aaactgtgag atg                            33

<210> SEQ ID NO 30
<211> LENGTH: 34
<212> TYPE: DNA
<213> ORGANISM: Artificial Sequence
<220> FEATURE:
<223> OTHER INFORMATION: Tf-AS1 primer
<220> FEATURE:
<223> OTHER INFORMATION: Synthesized

<400> SEQUENCE: 30
aattctcgag ttaaggtcta cggaaagtgc aggc                           34

<210> SEQ ID NO 31
<211> LENGTH: 36
<212> TYPE: DNA
<213> ORGANISM: Artificial Sequence
<220> FEATURE:
<223> OTHER INFORMATION: GS-FV-AS1 primer
<220> FEATURE:
<223> OTHER INFORMATION: Synthesized

<400> SEQUENCE: 31
ggatccgcct ccaccgggaa atggggctcg caggag                         36

<210> SEQ ID NO 32
<211> LENGTH: 40
<212> TYPE: DNA
<213> ORGANISM: Artificial Sequence
<220> FEATURE:
<223> OTHER INFORMATION: GS-Tf-S1 primer
<220> FEATURE:
<223> OTHER INFORMATION: Synthesized

<400> SEQUENCE: 32
ggtggaggcg gatccgtccc tgataaaact gtgagatggt                     40

<210> SEQ ID NO 33
<211> LENGTH: 48
<212> TYPE: DNA
<213> ORGANISM: Artificial Sequence
<220> FEATURE:
<223> OTHER INFORMATION: GS3-S primer
<220> FEATURE:
<223> OTHER INFORMATION: Synthesized

<400> SEQUENCE: 33
ccggtggagg cggttcaggc ggaggtggct ctggcggtgg cggatcca            48
```

```
<210> SEQ ID NO 34
<211> LENGTH: 48
<212> TYPE: DNA
<213> ORGANISM: Artificial Sequence
<220> FEATURE:
<223> OTHER INFORMATION: GS3-AS primer
<220> FEATURE:
<223> OTHER INFORMATION: Synthesized

<400> SEQUENCE: 34
acctccgcca gtccgcctc caccgagacc gccaccgcct aggtggcc                48

<210> SEQ ID NO 35
<211> LENGTH: 50
<212> TYPE: DNA
<213> ORGANISM: Artificial Sequence
<220> FEATURE:
<223> OTHER INFORMATION: GS-2 linker unit
<220> FEATURE:
<223> OTHER INFORMATION: Synthesized

<400> SEQUENCE: 35
tattagatct ggcggaggtg gctctggcgg tggcggatcc accggtatta              50

<210> SEQ ID NO 36
<211> LENGTH: 60
<212> TYPE: DNA
<213> ORGANISM: Artificial Sequence
<220> FEATURE:
<223> OTHER INFORMATION: dsGS1-T linker
<220> FEATURE:
<223> OTHER INFORMATION: Synthesized

<400> SEQUENCE: 36
aattaccggt ggaggcggat ccctggtgcc gcgcggcagc ggaggcggtt caaccggtat   60

<210> SEQ ID NO 37
<211> LENGTH: 58
<212> TYPE: DNA
<213> ORGANISM: Artificial Sequence
<220> FEATURE:
<223> OTHER INFORMATION: Helix linker S primer
<220> FEATURE:
<223> OTHER INFORMATION: Synthesized

<400> SEQUENCE: 37
aattaccggt gctgaagctg cagccaaaga agctgcagcc aaagaggccg cagctaag    58

<210> SEQ ID NO 38
<211> LENGTH: 46
<212> TYPE: DNA
<213> ORGANISM: Artificial Sequence
<220> FEATURE:
<223> OTHER INFORMATION: Helix linker AS primer
<220> FEATURE:
<223> OTHER INFORMATION: Synthesized

<400> SEQUENCE: 38
ttataccggt agcttttgct gcggcttcct tagctgcggc ctcttt                  46

<210> SEQ ID NO 39
<211> LENGTH: 31
<212> TYPE: DNA
<213> ORGANISM: Artificial Sequence
<220> FEATURE:
<223> OTHER INFORMATION: Albumin-S primer
<220> FEATURE:
<223> OTHER INFORMATION: Synthesized
```

```
<400> SEQUENCE: 39
gtgggatccg atgcacacaa gagtgaggtt g                              31

<210> SEQ ID NO 40
<211> LENGTH: 35
<212> TYPE: DNA
<213> ORGANISM: Artificial Sequence
<220> FEATURE:
<223> OTHER INFORMATION: Albumin-AS primer
<220> FEATURE:
<223> OTHER INFORMATION: Synthesized

<400> SEQUENCE: 40
cacggatccc tataagccta aggcagcttg acttg                          35

<210> SEQ ID NO 41
<211> LENGTH: 55
<212> TYPE: DNA
<213> ORGANISM: Artificial Sequence
<220> FEATURE:
<223> OTHER INFORMATION: oligonucleotide 1
<220> FEATURE:
<223> OTHER INFORMATION: Synthesized

<400> SEQUENCE: 41
gtgctcgagc gggggatctg gcgggtctgg aggctctgga gggtcgggag gctct     55

<210> SEQ ID NO 42
<211> LENGTH: 74
<212> TYPE: DNA
<213> ORGANISM: Artificial Sequence
<220> FEATURE:
<223> OTHER INFORMATION: oligonucleotide 2
<220> FEATURE:
<223> OTHER INFORMATION: Synthesized

<400> SEQUENCE: 42
caagggccct tatcaggatc ccgaccctcc agacccgcca gatccccag agcctccaga 60 gcctcccgac cctc                                                 74

<210> SEQ ID NO 43
<211> LENGTH: 33
<212> TYPE: DNA
<213> ORGANISM: Artificial Sequence
<220> FEATURE:
<223> OTHER INFORMATION: mut FVII(XhoI)-S primer
<220> FEATURE:
<223> OTHER INFORMATION: Synthesized

<400> SEQUENCE: 43
gagccccatt tccctcgagc ccagcagccc tgg                            33

<210> SEQ ID NO 44
<211> LENGTH: 33
<212> TYPE: DNA
<213> ORGANISM: Artificial Sequence
<220> FEATURE:
<223> OTHER INFORMATION: mut FVII(XhoI)-AS primer
<220> FEATURE:
<223> OTHER INFORMATION: Synthesized

<400> SEQUENCE: 44
ccagggctgc tgggctcgag ggaaatgggg ctc                            33

<210> SEQ ID NO 45
<211> LENGTH: 31
```

```
<212> TYPE: PRT
<213> ORGANISM: Artificial Sequence
<220> FEATURE:
<223> OTHER INFORMATION: GS linker (EP1816201)
<220> FEATURE:
<223> OTHER INFORMATION: Synthesized

<400> SEQUENCE: 45

Ser Ser Gly Gly Ser Gly Gly Ser Gly Gly Ser Gly Gly Ser Gly Gly
 1               5                  10                  15

Ser Gly Gly Ser Gly Gly Ser Gly Gly Ser Gly Gly Ser Gly Ser
             20                  25                  30

<210> SEQ ID NO 46
<211> LENGTH: 25
<212> TYPE: DNA
<213> ORGANISM: Artificial Sequence
<220> FEATURE:
<223> OTHER INFORMATION: Primer Nhe-Tf
<220> FEATURE:
<223> OTHER INFORMATION: Synthesized

<400> SEQUENCE: 46
aattgctagc atgaggctcg ccgtg                                    25

<210> SEQ ID NO 47
<211> LENGTH: 28
<212> TYPE: DNA
<213> ORGANISM: Artificial Sequence
<220> FEATURE:
<223> OTHER INFORMATION: Primer Tf-Age
<220> FEATURE:
<223> OTHER INFORMATION: Synthesized

<400> SEQUENCE: 47
aattaccggt aggtctacgg aaagtgca                                 28

<210> SEQ ID NO 48
<211> LENGTH: 25
<212> TYPE: DNA
<213> ORGANISM: Artificial Sequence
<220> FEATURE:
<223> OTHER INFORMATION: Primer Age-VII
<220> FEATURE:
<223> OTHER INFORMATION: Synthesized

<400> SEQUENCE: 48
aattaccggt gccaacgcgt tcctg                                    25

<210> SEQ ID NO 49
<211> LENGTH: 28
<212> TYPE: DNA
<213> ORGANISM: Artificial Sequence
<220> FEATURE:
<223> OTHER INFORMATION: Primer VII-Xho
<220> FEATURE:
<223> OTHER INFORMATION: Synthesized

<400> SEQUENCE: 49
aattctcgag ttagggaaat ggggctcg                                 28

<210> SEQ ID NO 50
<211> LENGTH: 32
<212> TYPE: DNA
<213> ORGANISM: Artificial Sequence
<220> FEATURE:
<223> OTHER INFORMATION: Primer TG del-S
<220> FEATURE:
```

<223> OTHER INFORMATION: Synthesized

<400> SEQUENCE: 50
cagcggaggc ggttcagtcc ctgataaaac tg    32

<210> SEQ ID NO 51
<211> LENGTH: 32
<212> TYPE: DNA
<213> ORGANISM: Artificial Sequence
<220> FEATURE:
<223> OTHER INFORMATION: Primer TG del-AS
<220> FEATURE:
<223> OTHER INFORMATION: Synthesized

<400> SEQUENCE: 51
cagttttatc agggactgaa ccgcctccgc tg    32

<210> SEQ ID NO 52
<211> LENGTH: 29
<212> TYPE: DNA
<213> ORGANISM: Artificial Sequence
<220> FEATURE:
<223> OTHER INFORMATION: Primer T del-S
<220> FEATURE:
<223> OTHER INFORMATION: Synthesized

<400> SEQUENCE: 52
cgagccccat ttcccggtgg aggcggatc    29

<210> SEQ ID NO 53
<211> LENGTH: 29
<212> TYPE: DNA
<213> ORGANISM: Artificial Sequence
<220> FEATURE:
<223> OTHER INFORMATION: Primer T del-AS
<220> FEATURE:
<223> OTHER INFORMATION: Synthesized

<400> SEQUENCE: 53
gatccgcctc caccgggaaa tggggctcg    29

<210> SEQ ID NO 54
<211> LENGTH: 6
<212> TYPE: PRT
<213> ORGANISM: Artificial Sequence
<220> FEATURE:
<223> OTHER INFORMATION: N-terminus restriction enzyme recognition
      sequence
<220> FEATURE:
<223> OTHER INFORMATION: Synthesized

<400> SEQUENCE: 54

Thr Gly Gly Gly Gly Ser
 1               5

<210> SEQ ID NO 55
<211> LENGTH: 6
<212> TYPE: PRT
<213> ORGANISM: Artificial Sequence
<220> FEATURE:
<223> OTHER INFORMATION: C-terminus restriction enzyme recognition
      sequence
<220> FEATURE:
<223> OTHER INFORMATION: Synthesized

<400> SEQUENCE: 55

Gly Gly Gly Ser Thr Gly
 1               5

```
<210> SEQ ID NO 56
<211> LENGTH: 4
<212> TYPE: PRT
<213> ORGANISM: Artificial Sequence
<220> FEATURE:
<223> OTHER INFORMATION: N-terminus of fusion partner

<400> SEQUENCE: 56

Asp Ala His Lys
 1
```